United States Patent
Kitamura

(10) Patent No.: US 7,387,619 B2
(45) Date of Patent: Jun. 17, 2008

(54) CAPACITANCE COUPLED SENSOR AND SUBSTANCE DETECTING METHOD USING CAPACITANCE-COUPLED SENSOR

(75) Inventor: Teruo Kitamura, Shizuoka (JP)

(73) Assignee: Aluvo Co., Ltd. (JP)

( * ) Notice: Subject to any disclaimer, the term of this patent is extended or adjusted under 35 U.S.C. 154(b) by 322 days.

(21) Appl. No.: 10/488,239

(22) PCT Filed: Jan. 21, 2002

(86) PCT No.: PCT/JP02/00377

§ 371 (c)(1),
(2), (4) Date: Mar. 2, 2004

(87) PCT Pub. No.: WO03/023332

PCT Pub. Date: Mar. 20, 2003

(65) Prior Publication Data

US 2004/0199131 A1   Oct. 7, 2004

(30) Foreign Application Priority Data

Sep. 4, 2001  (JP) ............................. 2001-267646

(51) Int. Cl.
*A61M 1/00* (2006.01)
*G01R 27/26* (2006.01)
(52) U.S. Cl. ...................... 604/319; 604/317; 604/318; 324/686
(58) Field of Classification Search ........ 604/317–319; 324/658–686
See application file for complete search history.

(56) References Cited

U.S. PATENT DOCUMENTS

| 4,099,167 | A | * | 7/1978 | Pomerantz et al. ......... 340/620 |
|---|---|---|---|---|
| 4,603,581 | A | | 8/1986 | Yamanoue et al. ........... 73/304 |
| RE34,601 | E | * | 5/1994 | Hochstein .................. 73/304 C |
| 6,426,227 | B1 | * | 7/2002 | Kritzman et al. ............. 436/43 |
| 2001/0038292 | A1 | * | 11/2001 | Nakayama et al. ......... 324/686 |

FOREIGN PATENT DOCUMENTS

| JP | 53-99973 | 8/1978 |
|---|---|---|
| JP | 58-7503 | 1/1983 |
| JP | 60-169719 | 9/1985 |
| JP | 63-105760 | 5/1988 |
| JP | 4-313029 | 11/1992 |
| JP | 11-311562 | 9/1999 |

\* cited by examiner

*Primary Examiner*—Tatyana Zalukaeva
*Assistant Examiner*—Melanie J Hand
(74) *Attorney, Agent, or Firm*—Bacon & Thomas, PLLC

(57) ABSTRACT

To allow a DC voltage to be obtained as an output signal for higher versatility. A sensor unit 400 has three electrodes: a transmission electrode 401, a reception electrode 402 and a shielding electrode 403. The shielding electrode 403 shields the transmission electrode 401 and the reception electrode 402 from each other in terms of high-frequency and is constantly earthed. A high-frequency voltage is applied to the transmission electrode 401 from a high-frequency oscillation circuit 410. A high-frequency voltage depending upon the magnitude of the electrostatic capacity between the electrodes 401 and 4023 is outputted from the reception electrode 402. The high-frequency voltage outputted from the reception electrode 402 is converted into a DC voltage by a detection circuit 420. The presence or absence or the amount of a substance is determined based on the magnitude of the DC voltage produced in the detection circuit 420.

5 Claims, 25 Drawing Sheets

CAPACITANCE COUPLED SENSOR AND SUBSTANCE DETECTING METHOD USING CAPACITANCE-COUPLED SENSOR

FILED OF THE INVENTION

This invention relates to a capacitance-coupled sensor and a method for detecting a substance using the capacitance-coupled sensor.

BACKGROUND OF THE INVENTION

Among sensors, there are capacitance-coupled sensors, namely capacitance-coupled (electrostatic capacity) sensors using a condenser (capacitor). JP-A-2000-80703 discloses a sensor using a capacitance-coupled sensor for detecting the human body sitting on a toilet seat of a human body private part washing device. The sensor disclosed in the official gazette has a sensor unit comprising a detection electrode and an earth electrode for capacitive coupling, and a protection electrode interposed between the detection electrode and the earth electrode, and the electrodes are insulated from each other. The electrostatic capacity between the detection electrode and the earth electrode is used to set the oscillation frequency of a high-frequency oscillator, and a change in the electrostatic capacity caused by approach of a human body is obtained as a change in the oscillation frequency (final output signal) from the oscillation circuit. The protection electrode is provided to reduce the electrostatic capacity possessed by the sensor itself.

However, the sensor disclosed in the official gazette requires a special device for detecting frequency since the output signal obtained from it a signal representing a change in frequency, which is not common. Also, the sensor disclosed in the official gazette is to detect the presence or absence of a substance that is a human body and is not intended to detect changes in the amount of a substance such as a liquid in a continuously variable manner.

This invention has been made in view of the above circumstances and it is, therefore, an object of this invention to provide a capacitance-coupled sensor from which a general DC voltage signal is obtained and a method for detecting a substance using the capacitance-coupled sensor.

DESCRIPTION OF THE INVENTION

In accomplishing the above object, a transmission electrode and a reception electrode adapted to be capacitively coupled to each other are used as an electrical resistance for a high-frequency voltage in this invention. To prevent the high-frequency voltage from leaking between the transmission electrode and the reception electrode, a shielding electrode is interposed between the transmission electrode and the reception electrode. A high-frequency voltage as an output from the reception electrode is converted into a DC voltage by detection.

More specifically, the following solution is adopted in the device of this invention. Namely, as described in claim 1, the capacitance-coupled sensor comprises:

a sensor unit having a transmission electrode, a reception electrode capacitively couplable to the transmission electrode, and a shielding electrode interposed between the transmission electrode and the reception electrode for shielding the transmission electrode and the reception electrode from each other, a high-frequency oscillator interposed between the transmission electrode and the shielding electrode for applying a high-frequency voltage to the transmission electrode; and a detector interposed between the reception electrode and the shielding electrode for converting a high-frequency voltage outputted from the reception electrode into a DC voltage.

The electrostatic capacity between the transmission electrode and the reception electrode differs depending upon whether there is a substance across the electrodes, and the difference in the electrostatic capacity can be obtained based on the magnitude of a DC voltage detected by the detector (to determine the presence or absence of the substance). When the amount of a substance existing across the transmission electrode and the reception electrode changes, the electrostatic capacity between the electrodes varies. The variation of the electrostatic capacity can be obtained based on the magnitude of a DC voltage detected by the detector (to determine the amount of the substance).

The following solutions can be combined with above solution as the base.

The capacitance-coupled sensor may further comprise a comparator for comparing an output voltage from the detector with a specified threshold voltage and outputting the comparison result. In this case, the presence or absence of the substance can be determined more easily based on the output from the comparator.

The capacitance-coupled sensor may further comprise an insulating wall member having an inner surface with which a substance comes into contact, wherein the sensor unit is provided on an outer surface of or in the wall member. In this case, the sensor unit does not have to be brought into contact with the substance.

The wall member may serve as a wall member of a vessel or a piping system. In this case, the presence or absence of a substance in the vessel or the piping system can be detected without bringing the sensor unit into contact with the substance.

The sensor unit may be constituted of at least three conductive wires extending in parallel to each other at small intervals as a whole. In this case, the electrodes can be formed of conductive wires with ease and the substance can be passed through the gaps between the electrodes.

The capacitance-coupled sensor may be configured as follows:

the plurality of conductive wires are divided into first to third groups each having a plurality of conductive wires, a plurality of conductive wires in the first group serving as a plurality of transmission electrodes, a plurality of conductive wires in the second group serving as a plurality of reception electrodes, and a plurality of conductive wires in the third group serving as a plurality of shielding electrodes, the conductive wires serving as shielding electrodes being arranged between each of conductive wires serving as transmission electrodes and each of the conductive wires serving as reception electrodes, the conductive wires serving as transmission electrodes being electrically connected with each other at one end, the conductive wires serving as the reception electrodes being electrically connected with each other at one end, and the conductive wires serving as shielding electrodes being electrically connected with each other at one end. In this case, the area for detecting the substance can be widened with a simple structure. Also, the number of electrical connections to the sensor unit can be the requisite minimum of three.

Each of the conductive wires is coated with an insulating coating material. In this case, the insulation between the conductive wires can be easily achieved. Also, the sensor unit can be formed using a commercially available coated wire with ease.

The capacitance-coupled sensor may further comprise spacer members provided at both longitudinal ends of the conductive wires for maintaining the intervals between the conductive wires. In this case, the conductive wires can be reliably kept separated at specified intervals.

The capacitance-coupled sensor may be configured as follows:

each of the transmission electrode, the reception electrode and the shielding electrode is constituted of a plurality of conductive wires, the plurality of conductive wires constituting the transmission electrode extending in parallel to each other at specified intervals on a first plane, the plurality of conductive wires constituting the reception electrode being located on a second plane generally parallel to the first plane and extending in a direction crossing the conductive wires constituting the transmission electrode at small intervals, the plurality of conductive wires constituting the shielding electrode being located between the first and second planes and extending in a direction crossing the plurality of conducive wires constituting the transmission electrode and the plurality of conducive wires constituting the reception electrode, whereby the conductive wires constituting the transmission electrode, the conductive wires constituting the reception electrode, and the conductive wires constituting the shielding electrode are mutually crossed at a multiplicity of points as seen in a direction perpendicular to the first plane so that the sensor unit can be in the form of a sheet with a multiplicity of mesh apertures as a whole. In this case, the area for detecting the substance can be significantly widened with a simple structure. Also, a multiplicity of detection sections each comprising a transmission electrode, a reception electrode and a shielding electrode can be formed.

The capacitance-coupled sensor may be configured as follows:

the conductive wires constituting the transmission electrode are electrically connected to each other at one end, the conductive wires constituting the reception electrode are electrically connected to each other at one end, and the conductive wires constituting the shielding electrode are electrically connected to each other at one end. In this case, the number of electrical connections to the sensor unit can be the requisite minimum of three.

The capacitance-coupled sensor may be configured as follows:

when the plurality of conductive wires constituting the transmission electrode, the plurality of conductive wires constituting the reception electrode and the plurality of conductive wires constituting the shielding electrode are represented as first to third conductive wire group, respectively, two of the first to third conductive wire groups extend perpendicular to each other and the other conductive wire group extends at an angle of about 45° to the two conductive wire groups. This feature is useful to improve the diagonal strength of the sensor unit having a net or lattice structure while securing its lateral and longitudinal strength.

Each of the conductive wires may be coated with an insulating coating material. In this case, the insulation between the electrodes can be achieved with ease using a commercially available coated wire.

The capacitance-coupled sensor may further comprise spacer members provided at both longitudinal ends of the conductive wires for maintaining the intervals between the conductive wires. This feature is useful to maintain the intervals, in other words, the positional relations, between the conductive wires reliably.

The capacitance-coupled sensor may be configured as follows:

the spacer members are arranged in the form of a ring with a large opening in the center, and the conductive wires extend across the opening of the spacer members with their longitudinal ends fixed to the spacer members. In this case, it is possible to secure sufficient rigidity of the spacer members with a simple structure. Also, it is advantageous that the spacer members do not interfere with the substance passing through the gaps (mesh apertures) among the conductive wires.

The capacitance-coupled sensor may further comprise a vessel for containing a substance, wherein the sensor unit is elongated in the direction in which the level of the substance in the vessel changes, and at least the part of the vessel where the sensor unit is located and around it have insulation. In this case, the amount of the substance in the vessel can be detected in a continuously variable manner.

The sensor unit may be provided on an outer surface of or in a wall of the vessel. In this case, the amount of the substance in the vessel can be detected without bringing the sensor unit in contact with the substance.

The sensor unit may be located outside and in the vicinity of the vessel. In this case, the amount of the substance in the vessel can be detected without directly attaching the sensor unit to the vessel.

The capacitance-coupled sensor may be configured as follows:

a plurality of sensor units are provided, transmission electrodes of the sensor units are connected in parallel to the high-frequency oscillator, reception electrodes of the sensor units are connected in parallel to the detector, and a selection unit for selectively connecting one of the transmission electrode to the high-frequency oscillator is provided. In this case, only one high-frequency oscillator and only one detector are required for the plurality of the sensor units.

The capacitance-coupled sensor may be configured as follows:

a plurality of sensor units are provided, transmission electrodes of the sensor units are connected in parallel to the high-frequency oscillator, reception electrodes of the sensor units are connected in parallel to the detector, and a selection unit for selectively connecting one of the reception electrode to the detector is provided. In this case, only one high-frequency oscillator and only one detector are required for the plurality of the sensor units.

The transmission electrode, the reception electrode and the shielding electrode may be supported by a support of an insulating synthetic resin. In this case, the attachment of the electrodes can be made using the support with the electrodes maintained in a specified positional relation.

The capacitance-coupled sensor may be configured as follows:

the transmission electrode, the reception electrode and the shielding electrode are so thin as to be able to be bent easily, and the support is flexible so that it can be bent easily together with the transmission electrode, the reception electrode and the shielding electrode. In this case, the electrodes, namely the support, can be attached to a curved surface or the like with ease.

The capacitance-coupled sensor may be configured as follows:

the transmission electrode, the reception electrode and the shielding electrode are embedded in the support, and conductive wires extending from the transmission electrode, reception electrode and shielding electrodes extend out of the support. This feature is useful to protect the electrode, in other words, to improve the service lives of the electrodes. Connections to the electrodes can be made using the conductive wires extending out of the support with ease.

The high-frequency oscillator may be a clock incorporated in a computer. In this case, the clock of the computer can be effectively used as the high-frequency oscillator.

The substance may be a living body, excrement of a living body, gas, liquid, solid matter, powder, particulate matter or gelatinous substance. The substances listed above are only example and the range (types) of substances as detecting objects is vary wide.

The capacitance-coupled sensor may further comprise an excrement cup to be attached to a patient for receiving excrement of the patient, wherein the sensor unit is provide on an outer surface of the excrement cup or an outer surface of an excrement discharge passage extending from the excrement cup. In this case, detection of the excrement can be performed while reliably preventing the sensor from being contaminated by the excrement.

The capacitance-coupled sensor may further comprise an excrement cup to be attached to a patient for receiving at least excrement of the patient, and a stool discharge passage for discharging at least stool from the excrement cup with an in-cup opening which opens upward in the excrement cup, wherein the sensor unit is placed across the in-cup opening so that stool excreted by the patient can be received by the sensor unit, and the stool on the sensor unit is passed through the sensor unit when the stool discharge passage is subjected to suction. In this case, the excrement excreted into the excrement cap can be reliably detected by the sensor unit having a wide detection area. Also, stool excreted into the excrement cup is pulverized by being passed through gaps among the conductive wires constituting the sensor unit and pulverized. This feature is useful to prevent the stool from clogging in the discharge passage.

In accomplishing the above object, this invention adopts the following solution. The method of this invention is the method for detecting a substance using a capacitance-coupled sensor comprising a sensor unit having a transmission electrode, a reception electrode adapted to be capacitively coupled to the transmission electrode, and a shielding electrode interposed between the transmission electrode and the reception electrode for shielding the transmission electrode and the reception electrode from each other, comprising the steps of:

applying a high-frequency voltage across the transmission electrode and the reception electrode, converting a high-frequency voltage outputted from the reception electrode into a DC voltage, and detecting at least either of the presence or absence or the amount of the substance based on the magnitude of the DC voltage.

The presence or absence or the amount of the substance can be thereby detected with ease based on the magnitude of the DC voltage.

According to this invention, it is possible to detect the presence or absence or the amount of a substance can be obtained vary easily based on the magnitude of a DC voltage and provide a sensor with high versatility.

BEST MODE FOR CARRYING OUT THE INVENTION

Description of FIG. 1 to FIG. 5

Figure 1:
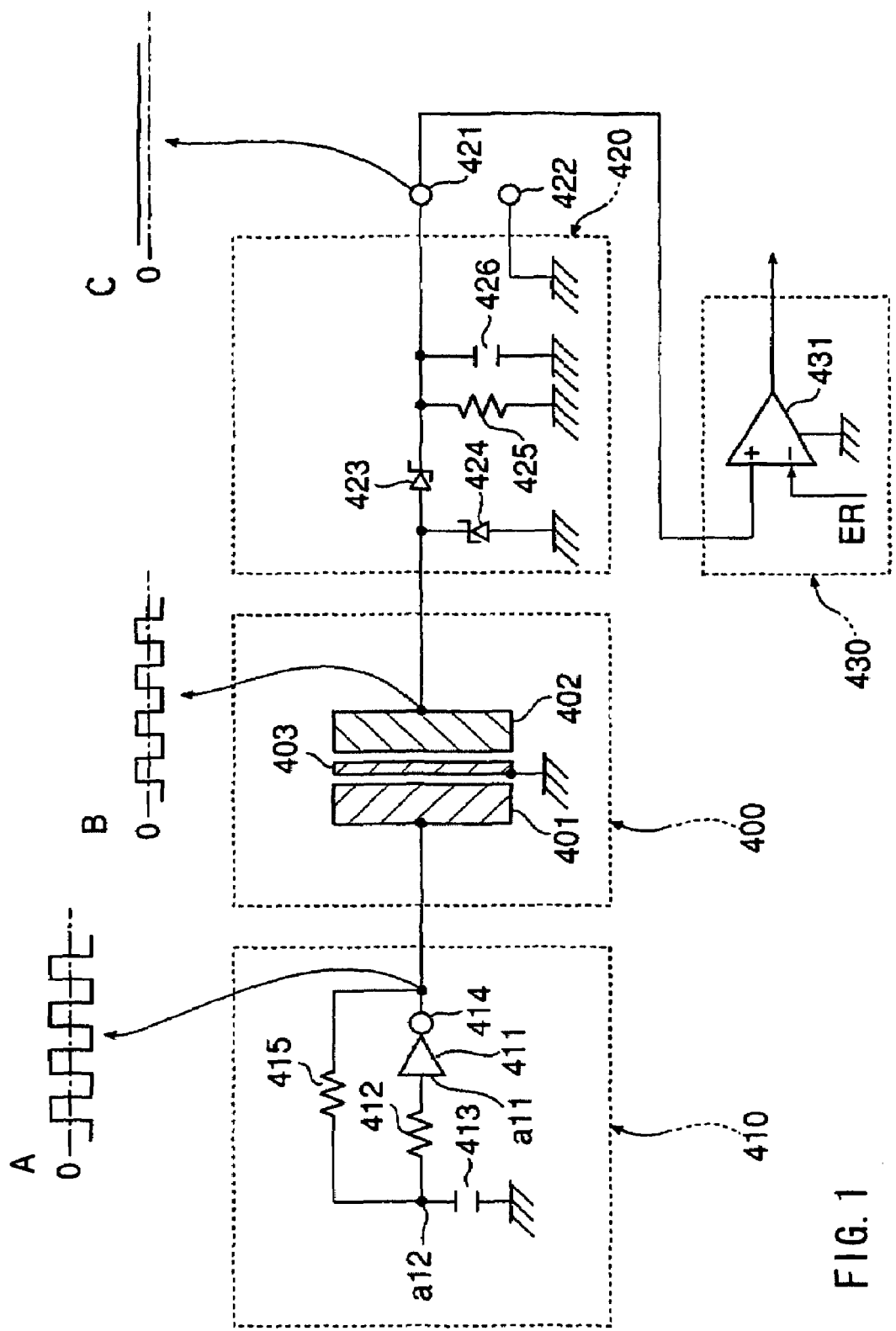
FIG. 1 is a view illustrating an example of a circuit of a capacitance-coupled sensor according to this invention.

FIG. 1 shows an example of a circuit of a capacitance-coupled sensor according to this invention. Designated as 400 is a sensor unit. The sensor unit 400 has three electrodes: a transmission electrode 401, a reception electrode 402 and a shielding electrode 403. The electrodes 401 to 403 are made of a conductive material (such as a thin plate of copper). The electrodes 401 to 403 are arranged in parallel to each other at specified small intervals. Namely, the space between the transmission electrode 401 and the shielding electrode 403, and the space between the reception electrode 402 and the shielding electrode 403 form insulating layers (an insulating material may be interposed between the electrodes for insulation).

The transmission electrode 401 and the reception electrode 402 are adapted to be capacitively coupled to each other and constitute a capacitor in conjunction with each other. The shielding electrode 403 shields the transmission electrode 401 and the reception electrode 402 from each other in terms of high-frequency as described later and is constantly earthed.

A high-frequency voltage (a voltage with a frequency of, for example, 2 MHz) is applied to the transmission electrode 401 from a high-frequency oscillation circuit (high-frequency oscillation unit, high-frequency oscillation means) 410. Namely, the high-frequency oscillation circuit 410 is formed between the transmission electrode 401 and the shielding electrode 403. A high-frequency voltage is outputted from the reception electrode 402 as described later. The high-frequency voltage outputted from the reception electrode 402 is converted into a DC voltage by a detection circuit (detection unit, detection means) 420 formed between the reception electrode 402 and the shielding electrode 403. The DC voltage outputted from the detection circuit 420 can be taken out as a potential difference between output terminals 421 and 422 (422 is an earth terminal).

The DC voltage produced by the detection circuit 420 is inputted into a comparison circuit (comparison unit, comparison means) 430 when necessary. The comparison circuit 430 comprises a comparator 431, which compares an inputted DC voltage with a specified threshold voltage ER and outputs a signal (ON signal or OFF signal) based on the result of the comparison. The comparison circuit 430 (comparator 431) is preferably used in detecting the presence or absence of a substance and may be omitted in detecting the amount of a substance in a continuously variable manner.

The high-frequency oscillation circuit 410 has a Schmitt circuit (hysteresis comparator) 411. The Schmitt circuit 411 outputs a specified fixed voltage +Eo when the input voltage into its input port a11 becomes a specified upper limit threshold voltage EH or higher. The Schmitt circuit 411 outputs a specified fixed voltage −Eo when the input voltage into its input port a11 becomes a specified lower limit threshold voltage EL or lower (0<EL<EH<Eo). The input port a11 is earthed via a buffering resistor 412 and a capacitor 413. The output voltage from the Schmitt circuit 411 is inverted by an inverter 414 and applied to the transmission electrode 401. The output voltage after having been inverted by the inverter 414 is returned to a feedback position a12 between the resistor 412 and the capacitor 413 via a feedback resistor 415.

Figure 2:
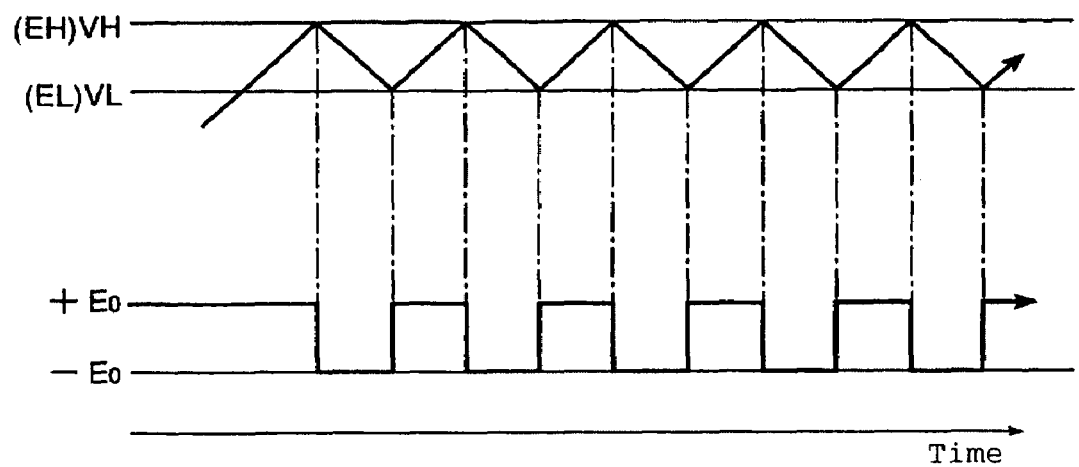
FIG. 2 is a graph schematically illustrating the manner of high-frequency oscillation of a high-frequency oscillator shown in FIG. 1.

Let VH be the voltage at the feedback position a12 at the time when the voltage at the input port a11 is the upper limit threshold voltage EH. Let VL be the voltage at the feedback position a12 at the time when the voltage at the input port a11 is the lower limit threshold voltage EL. In this case, since the voltage at the feedback position 12a varies between VH and VL, the output voltage from the Schmitt circuit 411 is in the form of square waves (high-frequency voltage) which varies between +Eo and −Eo as shown in FIG. 2. In FIG. 1, a power source circuit for operating the Schmitt circuit 411 is not shown.

The reason why the square waves as shown in FIG. 2 are obtained is described. When the operation of the Schmitt circuit 411 is started from the initial state where the capacitor 413 has been discharged (the voltage at the feedback position a12 is zero), the Schmitt circuit 411 outputs −Eo. The output voltage of −Eo outputted from the Schmitt circuit 411 is inverted into +Eo by the inverter 414. The output voltage of +Eo from the inverter 414 is applied to the capacitor 413 via a feedback resistor 415, whereby the capacitor 413 starts charging and the voltage at the feedback position a12 is gradually increased. When the voltage at the feedback position a12 is increased to VH, the Schmitt circuit 411 outputs +Eo. When the Schmitt circuit 411 outputs +Eo, since the output of the inverter 414 becomes −Eo, the charged capacitor 413 start discharging to the feedback resistor 415. By gradual discharge of the capacitor 413, the voltage at the feedback position a12 is gradually decreased to VL. The Schmitt circuit 411 thereby outputs −Eo. When the capacitor 413 is repeatedly charged and discharged as described above, the voltage at the feedback position a12 varies between VH and VL, whereby the output of the Schmitt circuit 411 is varied between +Eo and −Eo (square waves).

As described above, when the transmission electrode 401 and the reception electrode 402 are capacitively coupled to each other while a high-frequency voltage is applied to the transmission electrode 401 (for example, when a substance such as a human approaches the transmission electrode 401 and the reception electrode 402), a high-frequency voltage is outputted from the reception electrode 402. The magnitude of the high-frequency voltage to be outputted from the reception electrode 402 depends upon the electrostatic capacity between the electrodes 401 and 402. The shielding electrode 403 prevents the high-frequency voltage applied to the transmitting electrode 401 from leaking directly to the reception electrode 402.

The detection circuit 420 has two Schottky barrier diodes 423 and 424, by which the high-frequency voltage outputted from the reception electrode 402 is subjected to voltage doubler rectification. The high frequency voltage after the voltage doubler rectification is smoothed into a DC voltage by the resistor 425 and a capacitor 426. In FIG. 1, "A" shows an example of the waveform of the high-frequency voltage applied to the transmission electrode 401. In FIG. 1, "B" shows an example of the waveform of the high-frequency voltage outputted from the reception electrode 402. In FIG. 1, "C" shows an example of the waveform after being smoothed into a DC voltage.

The comparison circuit 430 (comparator 431) compares the DC voltage (input voltage) outputted from the detection circuit 420 with the specified threshold voltage ER. The comparison circuit 430 outputs, for example, a specified ON signal only when the input voltage is higher than the threshold voltage ER.

Figure 3:
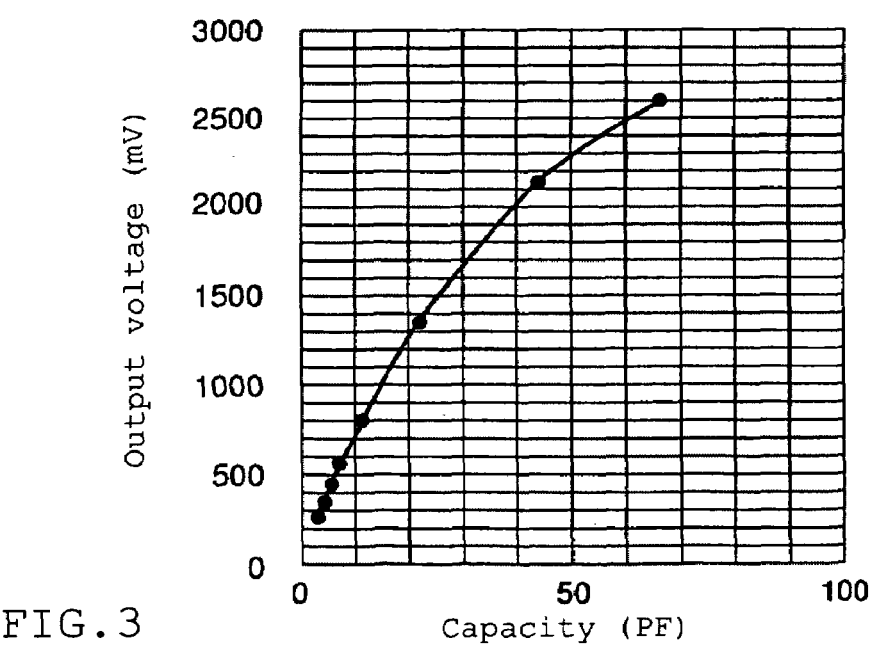
FIG. 3 is a characteristic curve showing the relation with the electrostatic capacity.
Figure 4:
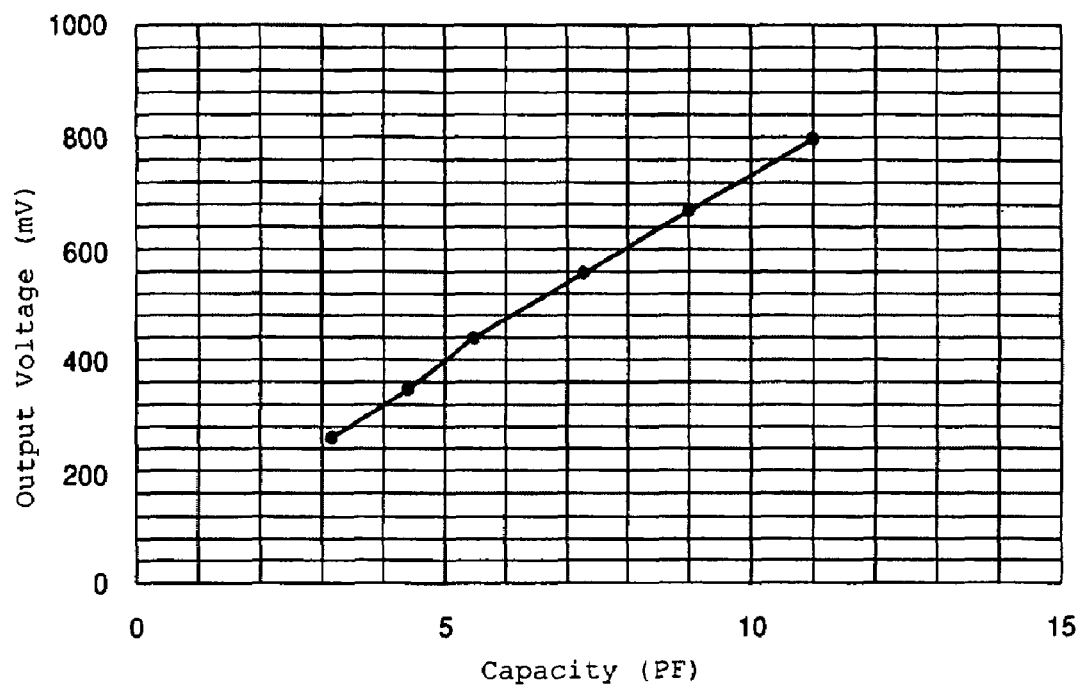
FIG. 4 is an enlarged view of a section of the characteristic curve shown in FIG. 3 where the electrostatic capacity is small.

FIG. 3 is a characteristic curve showing the relation between the magnitude of the electrostatic capacity between the transmission electrode 401 and the reception electrode 402 and the DC output voltage from the detection circuit 420 (the potential difference across the electrodes 421 and 422). As shown in FIG. 3, there is a non-linear relation between the electrostatic capacity and the DC output voltage as a whole. FIG. 4 shows the characteristic shown in FIG. 3 within a range where the electrostatic capacity is small. As is clear from FIG. 4, it is understood that there is a linear relation between the electrostatic capacity and the DC output voltage when the electrostatic capacity is small.

Figure 5:
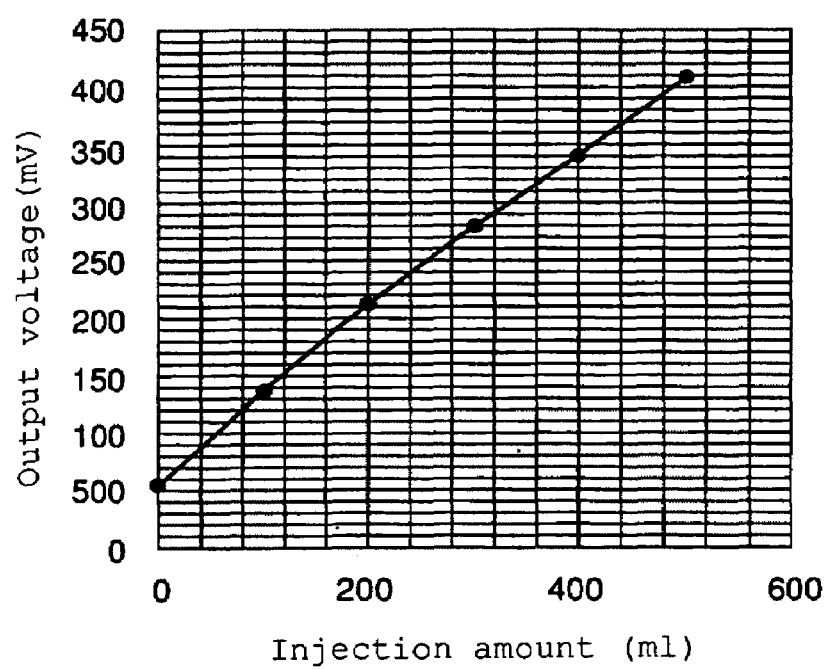
FIG. 5 is a characteristic curve showing an example of the relation between the amount of water in a measuring vessel and the output voltage.

FIG. 5 shows the relation between the amount of water in a commercially available measuring vessel of a (insulating) synthetic resin and the output voltage from the detection circuit 420 measured with the sensor unit 400 attached to an outer surface of the measuring vessel, as shown in FIG. 1. As is clear from FIG. 5, the amount of water in the measuring vessel can be obtained based on the output voltage. The sensor unit 400 (the electrodes 401 to 403 thereof) is placed such that it extends in the direction in which the level of water in the vessel moves (vertical direction).

Examples of the substance for capacitively coupling the transmission electrode 401 and the reception electrode 402 include a living body; excrement of a living body; liquids such as water, gasoline and chemical liquid; gases such as natural gas, hydrogen gas and manufactured gas; powders such as rice powder and flour; solid matters such as concrete products, wood products and synthetic resin products; particulate matters; and gelatinous substances. In other words, substances which do not capacitively couple the transmission electrode 401 and the reception electrode 402 are exceptional. Namely, this invention has wide industrial applications for detecting the presence or absence, or the amount of various types of substances. The sensor unit 400 may not be in contact with the substance to be detected (or may be used in contact therewith).

Figure 6:
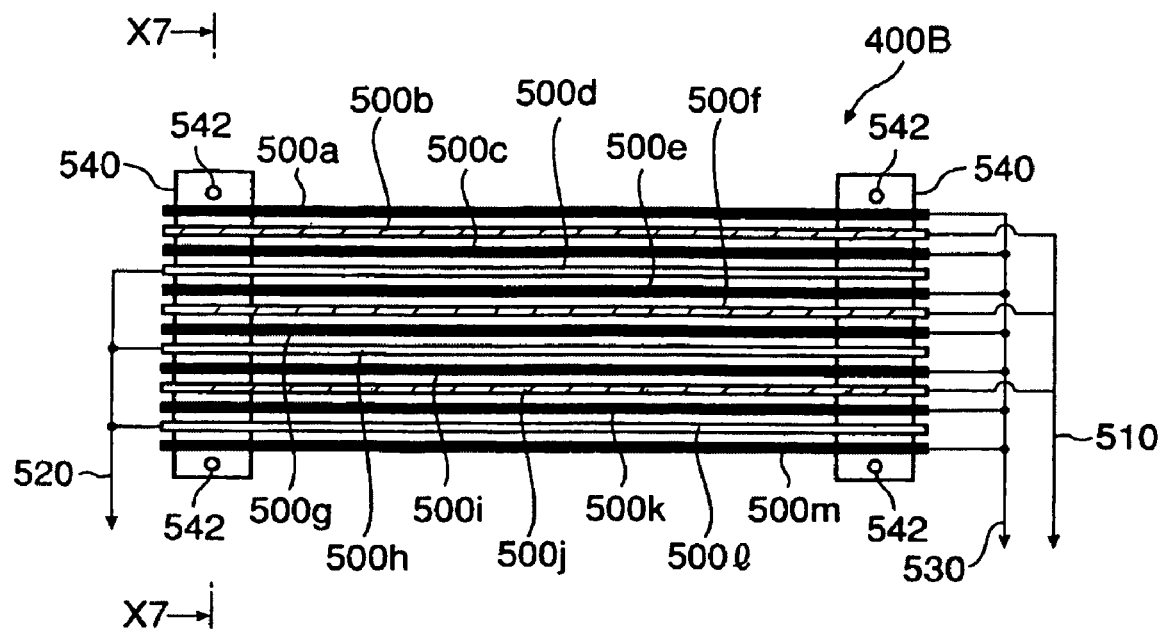
FIG. 6 is a plan view illustrating an example in which a plurality of conductive wires are arranged in parallel to form a sensor unit.
Figure 7:
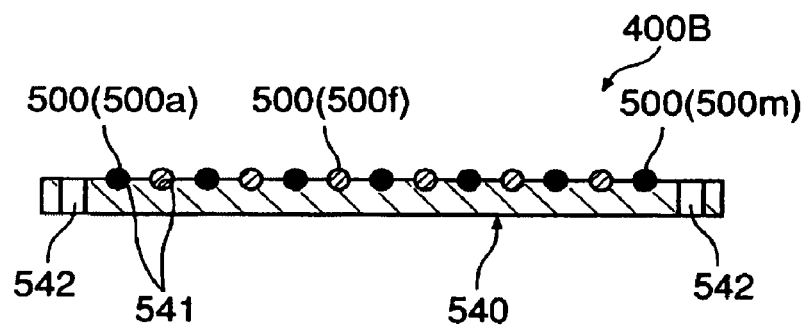
FIG. 7 is a cross-sectional view taken along the line X7-X7 in FIG. 6.
Figure 8:
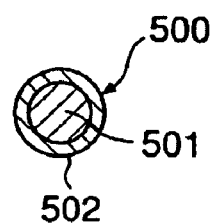
FIG. 8 is a cross-sectional view of the conductive wire.

Description of FIG. 6 to FIG. 8

FIG. 6 to FIG. 8 show a modification of the sensor unit 400. A sensor unit 400B in this example substantially has a plurality of sets of sensor unit 400 formed using a plurality of conductive wires 500. Each of the conductive wires 500 used comprises a conductive wire material 501 such as a copper wire coated entirely with a coating material 502 of a synthetic resin as an insulating material as shown in FIG. 8.

The plurality of conductive wires 500 are arranged almost in parallel to one another at small intervals. In this embodiment, thirteen conductive wires 500 are used in total. In FIG. 6, the conductive wires 500 are designated as 500*a*, 500*b*, . . . , and 500*m* from top to bottom for identification purpose. Among them, every other conductive wire in the arranging direction of the conductive wires, including the ones at the both ends, (the conductive wires 500*a*, 500*c*, 500*e*, 500*g*, 500*i*, 500*k* and 500*m*, shown in black for clarity) serve as shielding electrodes 403. The three conductivity wires 500*b*, 500*f*, 500*j* (shown with hatching for clarity) serve as transmission electrodes 401. The three conductivity wires 500*d*, 500*h*, 500*l* (shown in white for clarity) serve as reception electrodes 402. As described above, conductive wires serving as shielding electrodes are located between conductive wires serving as transmission electrodes and conductive wires serving as reception electrodes adjacent to each other. The conductive wires located on the outermost side in the arranging direction of the plurality of conductive wires also serve as shielding electrodes.

The plurality of (three in this embodiment) conductive wires 500*b*, 500*f* and 500*j* serving as transmission electrodes are electrically connected to each other at one end by a connection wire 510. The plurality of (three in this embodiment) conductive wires 500*d*, 500*h* and 500*l* serving as reception electrodes are electrically connected to each other at one end by a connection wire 520. The plurality of (seven in this embodiment) conductive wires 500*a*, 500*c*, 500*e*, 500*g*, 500*i*, 500*k* and 500*m* serving as shielding electrodes are electrically connected to each other at one end by a connection wire 530.

Both ends of the plurality of conductive wires 500 (500*a* to 500*m*) are fixed to spacer members 540. Each of the spacer members 540 is made of an insulating material (such as a synthetic resin) and has a surface with grooves 541 for receiving the conductive wires in an isolated manner (the number of the grooves 541 is the same as the number of the conductive wires). By the spacer members 540, the conductive wires 500 are kept separated at specified small intervals. The spacer members 540 have fixing holes 542 so that the sensor unit 400B can be fixed to a specified member using (the fixing holes 542 of) the spacer members 540.

The sensor unit 540B as described above is mainly used to detect the presence or absence of a substance. For example, it is provided in an excrement cup attached to a human body. In this case, stool or urine excreted by a patient comes into contact with a wire serving as a transmission electrode and a wire serving as a reception electrode simultaneously, the capacitive coupling is varied, whereby the presence of the stool or urine can be detected. Since sensor unit 540B substantially has a plurality of sets of sensor units 400, which are provided over a wide area, the stool or urine can be reliably detected. The sensor has various other applications. For example, it may be installed outdoors to detect rainfall.

At least the portion of the sensor unit 400B between the two spacer members 540 has flexibility. The spacer members 540 may be formed of a flexible material so that the entire portion of the sensor unit 400B can have flexibility.

Figure 9:
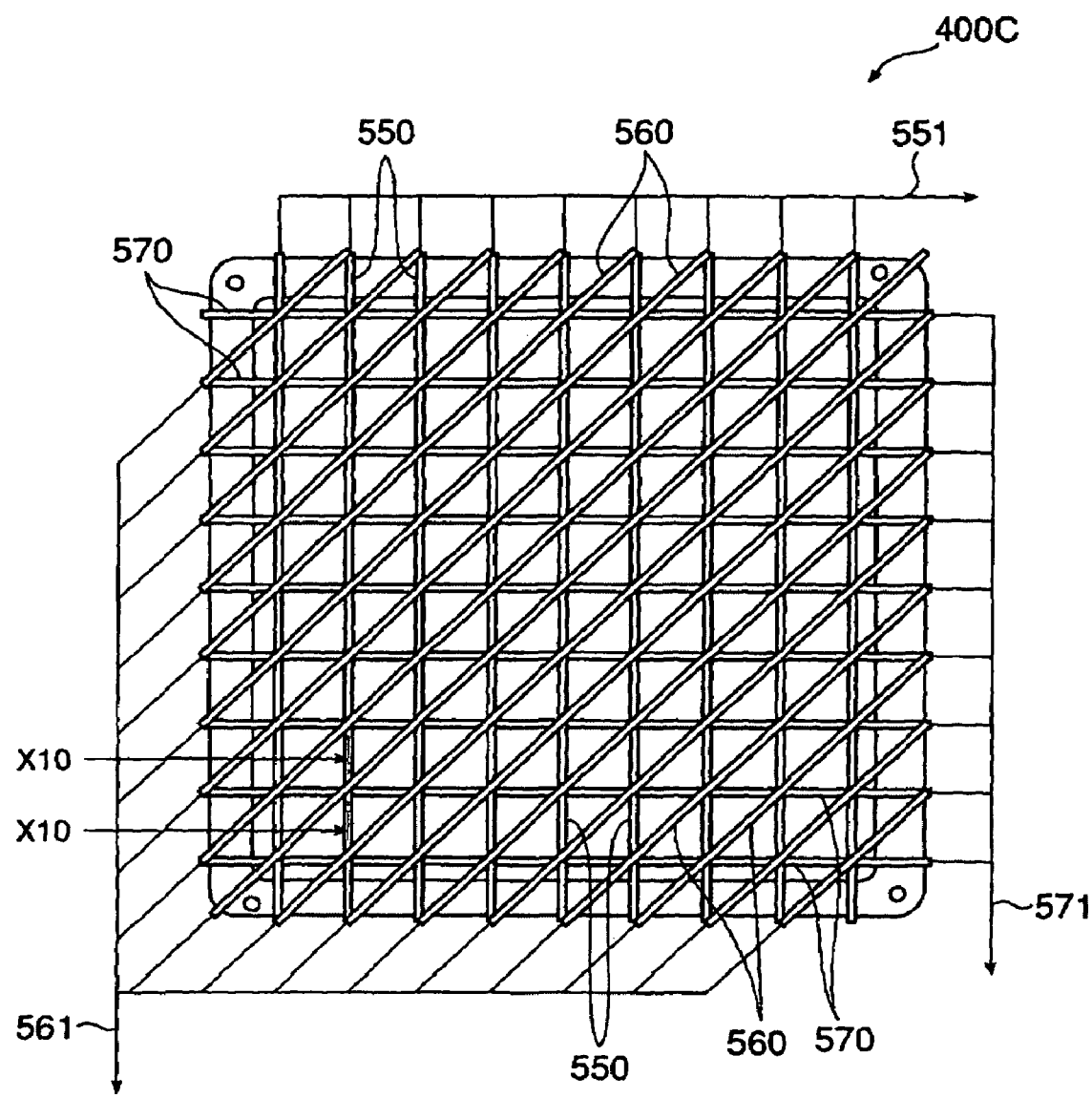
FIG. 9 is a plan view illustrating an example of a sensor unit comprising a plurality of conductive wires arranged in a net (lattice) structure.
Figure 10:
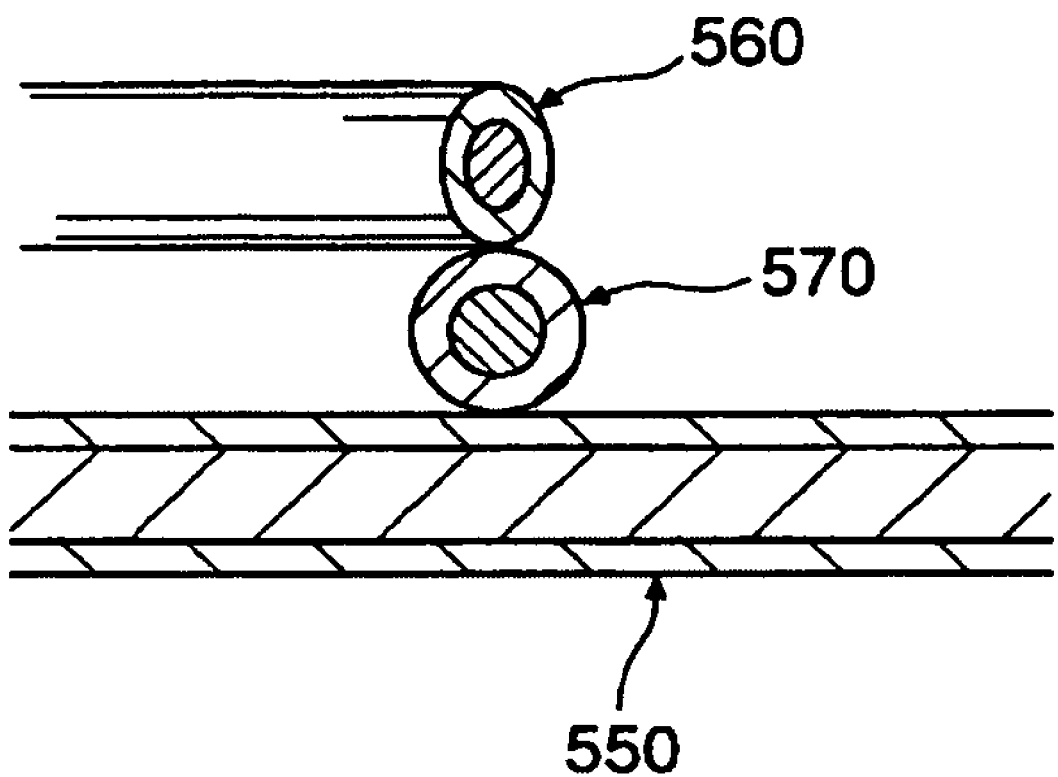
FIG. 10 is a cross-sectional view taken along the line X10-X10 in FIG. 9.

Description of FIG. 9 and FIG. 10

FIG. 9 and FIG. 10 show a modification of the sensor unit 400. A sensor unit 400C in this example substantially has a plurality of sets of sensor unit 400 formed using a plurality of conductive wires 500. Each of the conductive wires 500 used comprises a conductive wire material 501 such as a copper wire coated entirely with a coating material 502 of a synthetic resin as an insulating material as shown in FIG. 8 (the same as that in the example shown in FIG. 6 to FIG. 8).

In FIG. 9, conductive wires serving as transmission electrodes 401 are designated as 550, conductive wires serving as reception electrodes 402 are designated as 560, and conductive wires serving as shielding electrodes 403 are designated as 570 to distinguish the plurality of conductive wires 500. The conductive wires 550 serving as transmission electrodes are located on a specified plane (first plane, which is in parallel to the plane of FIG. 9) and extend generally in parallel to each other in the vertical direction of FIG. 9 at small intervals. The conductive wires 550 are electrically connected to each other at one end by a connection wire 551.

The conductive wires 570 serving as shielding electrodes are located on the conductive wires 550 serving as transmission electrodes (on a second plane, which is in parallel to the first plane) and extend generally in parallel to each other in the lateral direction of FIG. 9 at small intervals. The conductive wires 570 are electrically connected to each other at one end by a connection wire 571.

The conductive wires 560 serving as reception electrodes are located on the conductive wires 550 and 570 and extend in a diagonal direction of FIG. 9. In this embodiment, the conductive wires 560 extend at an angle of almost 45 degrees to the conductive wires 550 and 5780. The conductive wires 560 are electrically connected to each other at one end by a connection wire 561.

The conductive wires 550, 560 and 570 forms a multiplicity of intersections in a matrix manner as shown in FIG. 9 (plan view), and each of the multiplicity of intersections constitute a sensor unit 400. One of the intersections is shown in FIG. 10 in detail. At the intersections, the coating materials 502 of the conductive wires 550, 560 and 570 are fusion-bonded or bonded with an adhesive so that they can be integrated and cannot be displaced. As described above, the sensor unit 400C is in the form of a thin net or lattice sheet with a multiplicity of mesh apertures (gaps).

The sensor unit 400C has a spacer member 580 around it. The spacer member 580 is formed of an insulating material such as a synthetic resin. The spacer member 580 has a ring shape with a large opening 581 in the center as a whole (ring shape with almost square inner and outer periphery). The conductive wires 550, 560, and 570 extend across the opening 581. Both ends of the conductive wires 550, 560, and 570 are fixed to the spacer member 580 so that the conductive wires 550, 560, and 570 cannot be displaced.

The sensor unit 400C as described above can be used in the same manner as the sensor unit 400B shown in FIG. 6. Although not shown, the spacer member 580 may have fixing holes, or may have flexibility. The extending directions of the conductive wires serving as the electrodes shown in FIG. 8 are illustrative. The conductive wires may extend in any direction. For example, the conductive wire 550 serving as transmission electrodes and the conductive wires 560 serving as reception electrodes 560 may be perpendicular to each other, or the conductive wire 560 serving as reception electrodes and the conductive wires 570 serving as shielding electrodes 560 may be perpendicular to each other (as long as the conductive wires serving as shielding electrodes are located between the conductive wires serving as transmission electrodes and the conductive wires serving as receiving electrodes).

Figure 11:
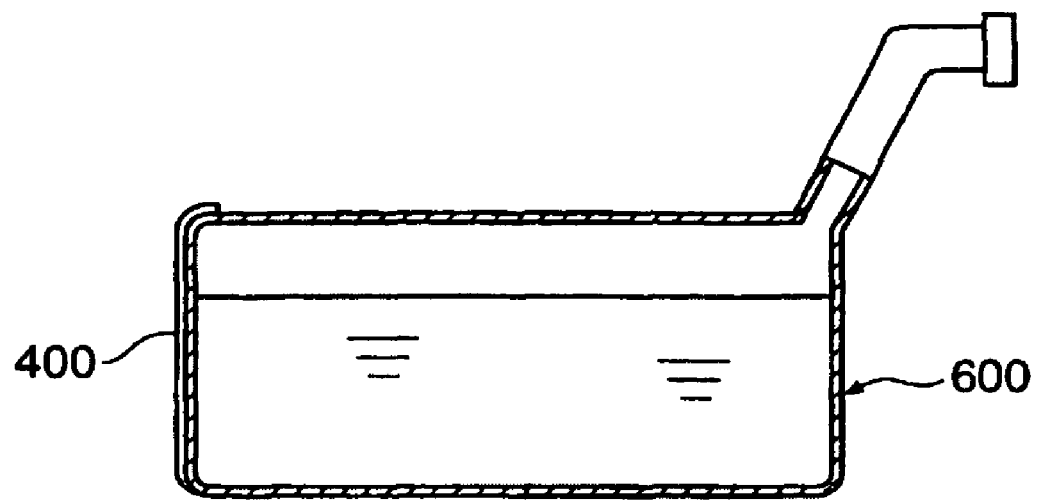
FIG. 11 is a simplified cross-sectional side view illustrating an example in which the sensor unit is provided on a fuel tank.
Figure 12:
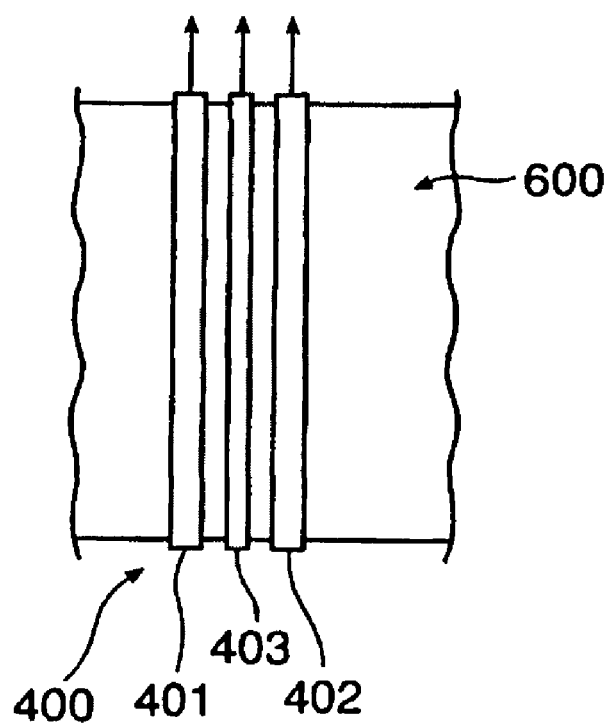
FIG. 12 is an enlarged left side view of FIG. 11.
Figure 13:
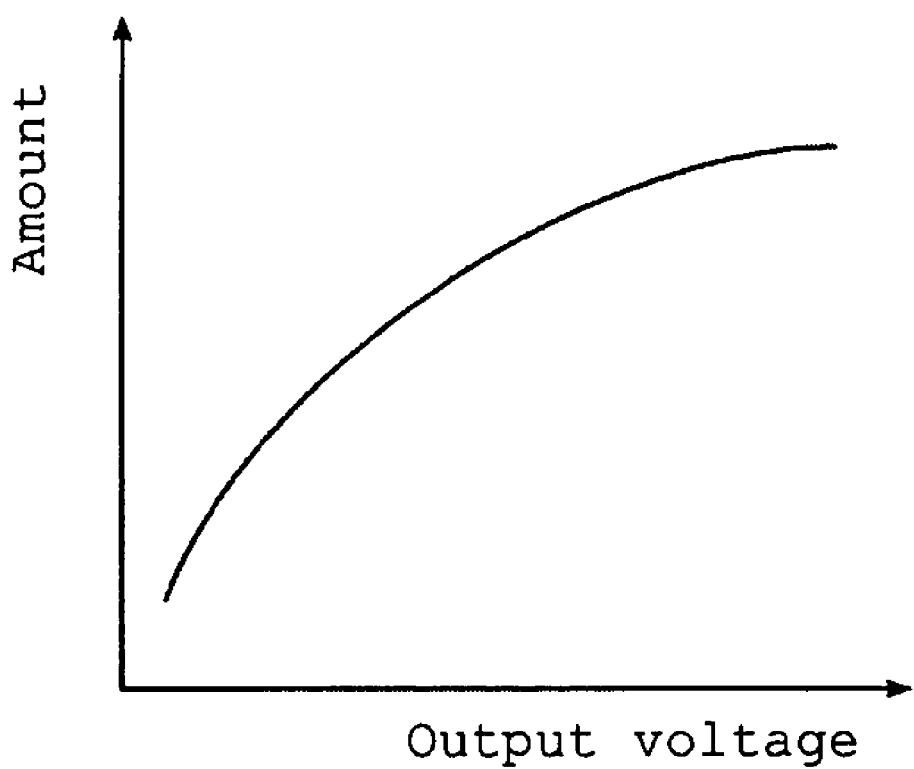
FIG. 13 is a characteristic curve showing the relation between the amount of fuel and the output voltage from a detection circuit.

Description of FIG. 11 to FIG. 13

FIG. 11 and FIG. 12 show an example in which the sensor unit 400 of the capacitance-coupled sensor shown in FIG. 1 is used to detect the amount of fuel in a fuel tank of a vehicle. A fuel tank 600 (wall members forming the exterior thereof) is made of a fiber-reinforced plastic as an insulating material. The sensor unit 400, which is elongated vertically, is attached along mist of the vertical length of an outer surface of the fuel tank 600. When the amount of fuel in the fuel tank 600 is changed, the electrostatic capacity between the transmission electrode 401 and the reception electrode 402 of the sensor unit 400 is changed, whereby the amount of fuel can be detected (based on the potential difference across the terminals 421 and 422 shown in FIG. 1).

When there is no linear relation between the magnitude of the output voltage and the amount of fuel in the example shown in FIG. 11, the relation therebetween is stored (in a recording medium such as a RAM) as a table as shown in FIG. 13 so that the amount of fuel can be determined by comparing the detected voltage with the table value (this is applicable not only to the detection of fuel amount but also to any case of detecting the amount of a substance).

Description of FIG. 14 to FIG. 17

Figure 14:
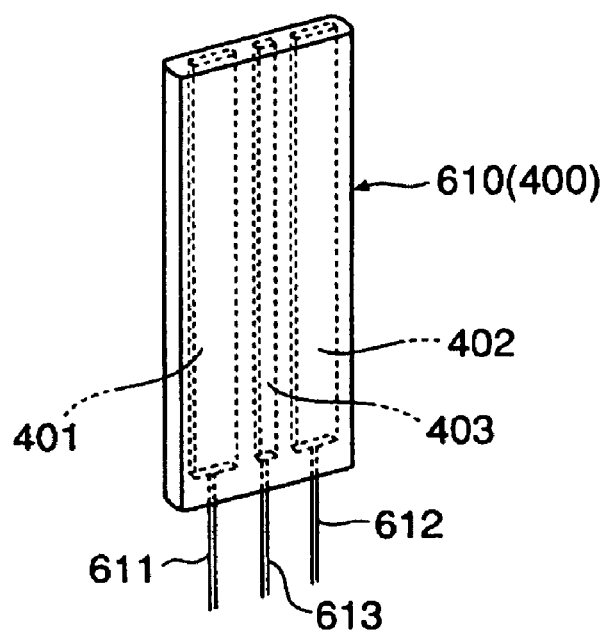
FIG. 14 is a perspective view illustrating an example in which electrodes are held in a support.
Figure 15:
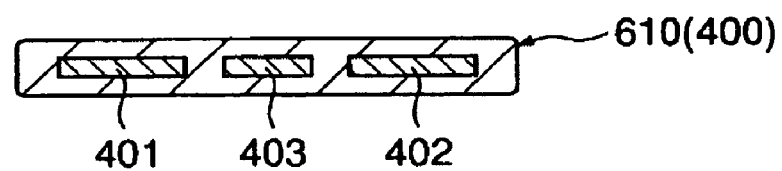
FIG. 15 is cross-sectional view of FIG. 14.

FIG. 14 and FIG. 15 show an example in which the sensor unit 400 (the electrodes 401, 402 and 403 thereof) is embedded in a support 610 of an insulating material such as a synthetic resin. Conductive wires 611, 612 and 613 extending from the electrodes 401, 402 and 403, respectively, extend out of the support 610. Since the sensor unit 400 is entirely covered, it has strength against external forces and is easy to attach since the attachment can be made via the support 610. The support 610 may be made of a flexible material so that the entire portion can have flexibility. The electrodes 401 to 403 and the support 610 can be made as thin as a film as a whole. When there is a possibility that a large voltage is used or large external forces are applied, or when the sensor must have durability for outdoor use, it is advisable to increase the coating thickness of the support 610. Only one side (upper side in FIG. 15, for example) surfaces of the electrodes 401 to 403 as the detection surfaces thereof may be exposed (to improve sensitivity).

Figure 16:
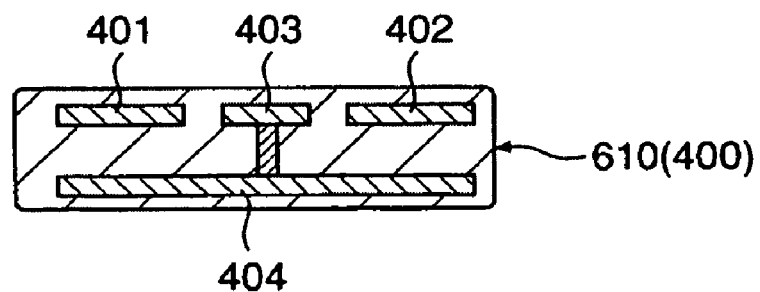
FIG. 16 is a cross-sectional view illustrating a modification of FIG. 15.

As shown in FIG. 16, an electrode 404 for preventing noise may be additionally embedded in the support 610. When one side of the support 610 (the upper side in FIG. 15) serves as a detection surface, the electrode 404 is located on the other side of the electrodes 401 to 403. The electrode 404 is electrically connected to the shielding electrode 403. When the electrode 404 for preventing noise is provided, it is possible to prevent capacitive coupling between the transmission electrode 401 and the reception electrode 402 at the time when a substance which is not a detecting object approaches the other side of the support 610. The electrode 404 for preventing noise may be used when the electrodes 401 to 403 are not supported in the support 610.

Figure 17:
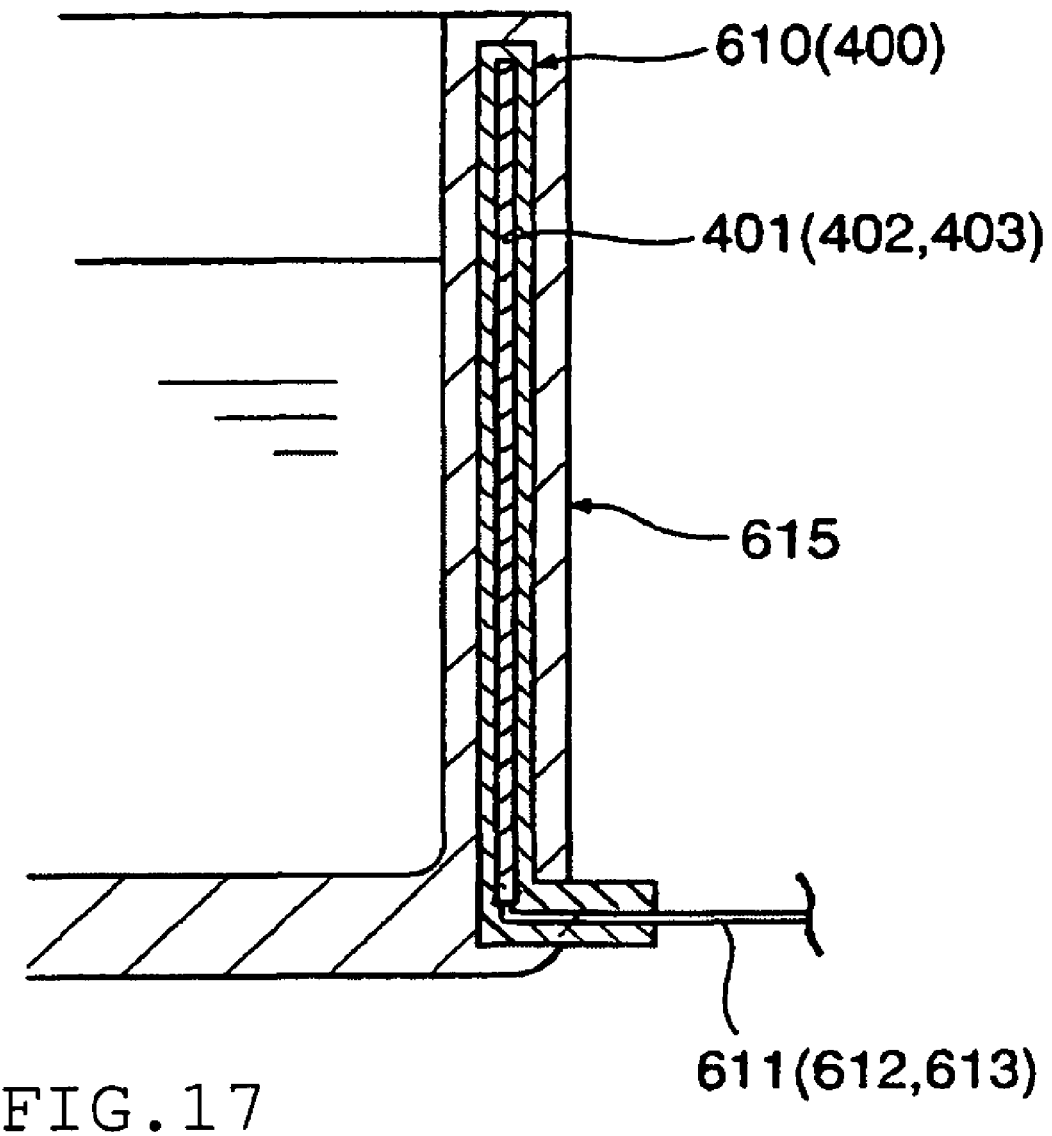
FIG. 17 is a cross-sectional view of an essential part of an example in which the support is embedded in a wall member of a vessel.

FIG. 17 shows an example in which the electrodes 401 to 403 supported in the support 610 is embedded in a wall member of a vessel 615 such as a measuring vessel. The wall members constituting the exterior of the vessel 615 are made of an insulating material such as a synthetic resin. When the part in which the support 610 (the electrodes 401 to 403) is located and around it have insulation, the vessel 615 may be made of any material. The electrodes 401 to 403, namely the support 610, can be embedded in forming the vessel 615 by injection molding.

Only the conductive wires 611 to 613 for the electrodes extend out of the wall member of the vessel 615. The electrodes 401 to 403 extend in the direction in which the level of the substance in the vessel 615 (liquid such as water) moves (in a vertical direction). The amount of the substance in the vessel 615 can be detected in a continuously variable manner based on the magnitude of the DC voltage outputted from the detection unit 420.

Description of FIG. 18 to FIG. 21

Figure 18:
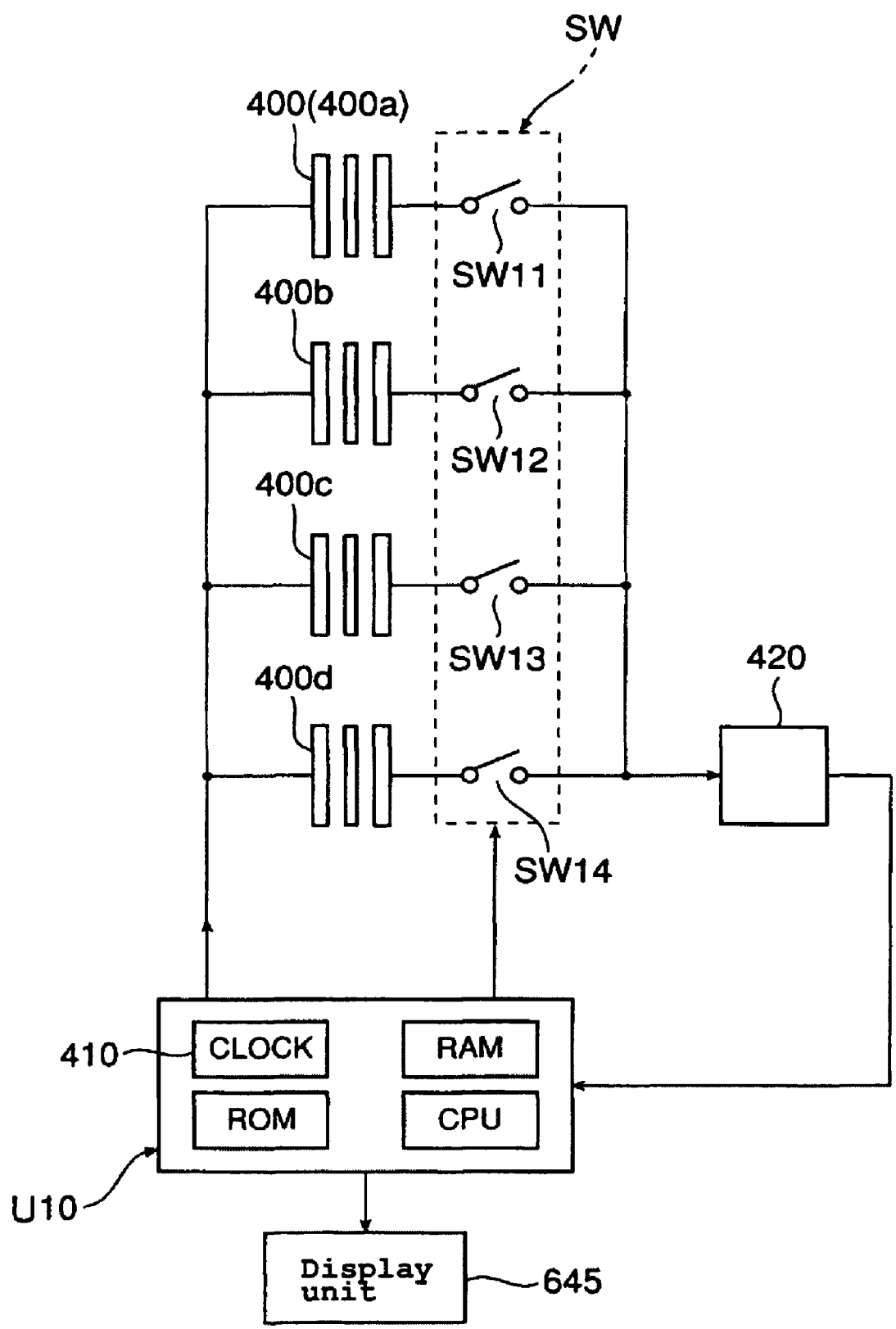
FIG. 18 is view illustrating an example of a circuit suitable for a sensor having a plurality of sensor units.

FIG. 18 shows an example suitable for a sensor having a plurality of sensor units 400, one high-frequency oscillation circuit 410 and one detection circuit 420. Namely, FIG. 18 shows an example in which the presence or absence or the amounts of substances can be independently detected by plural number of sensor units 400. In FIG. 18, designated as U10 is a controller constituted using a microcomputer. The controller U10 may be a personal computer. The high-frequency oscillation circuit 410 is constituted using (the oscillation frequency of) a clock of the controller U10 (amplifies the output from the clock and outputs it when necessary).

In this embodiment, there are four sensor units 400, which are designated as 400a, 400b, 400c and 400d for identification purpose. The sensor units 400 (400a to 400d) are connected in parallel to each other to the clock constituting the high-frequency oscillation circuit 410 in the controller U10. The sensor units 400 (400a to 400d) are connected in parallel to each other to the detection circuit 420. Electromagnetic switches SW11, SW12, SW13 and SW14 are connected between each of the sensor units 400 and the detection circuit 420. The switches SW11 to SW14 are independently opened and closed by the controller U10 (when one of the switches is turned on, the other switches are turned off). The switches SW11 to SW14 constitutes a selection unit SW (selection means).

When only the switch SW11 is turned on by the controller U10, only the sensor unit 400a provides an output to the detection circuit 420, whereby the presence or absence or the amount of the substance as a detecting object of the sensor unit 400a is detected. When only the switch SW12 is turned on, the presence or absence or the amount of the substance as a detecting object of the sensor unit 400b is detected. When only the switch SW13 is turned on, the presence or absence or the amount of the substance as a detecting object of the sensor unit 400c is detected. When only the switch SW14 is turned on, the presence or absence or the amount of the substance as a detecting object of the sensor unit 400d is detected. The number of the sensor units 400 can be arbitrarily determined. The presence or absence or the amount of the substance detected can be displayed on a display unit 645.

As a modification of the device shown in FIG. 18, the selection unit SW may be provided between the plurality of sensor units 400 (400a to 400d) and the high-frequency oscillation circuit 410. Also in this case, by turning on one of the switches, the presence or absence or the amount of the substance as the detecting object of the sensor unit corresponding to the switch turned on is detected.

Figure 19:
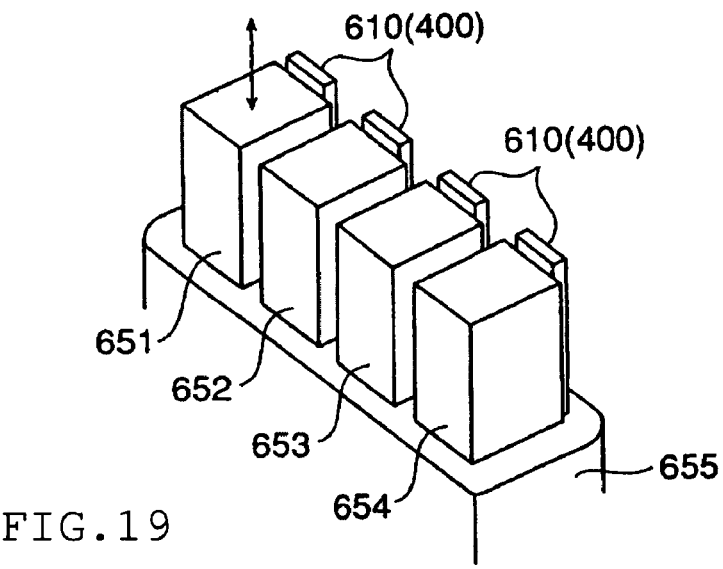
FIG. 19 is a perspective view of an essential part of an example in which the amounts of inks in a plurality of ink tanks are individually detected.
Figure 20:
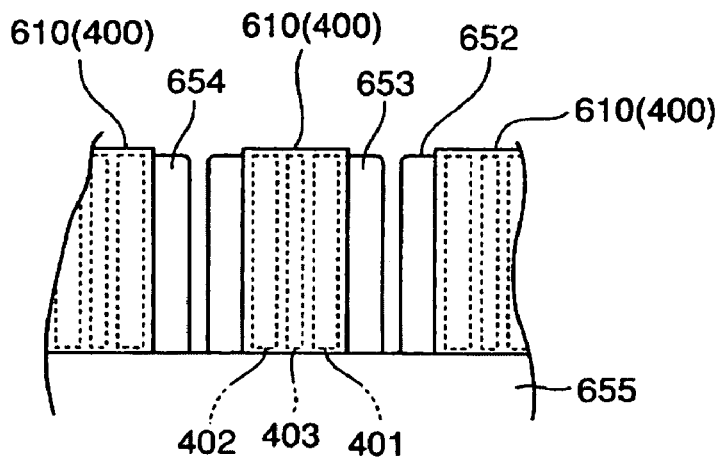
FIG. 20 is a backside view of FIG. 19, looking from the side of supports.
Figure 21:
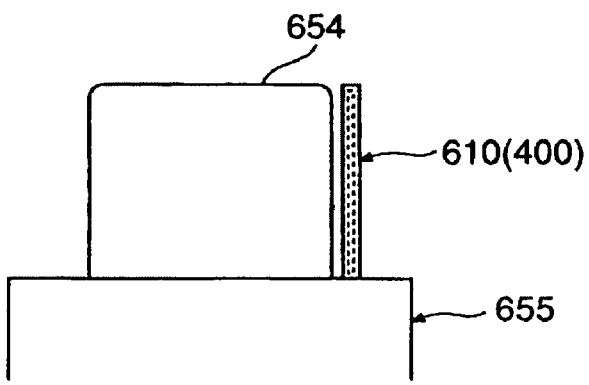
FIG. 21 is a side view of FIG. 19, looking in the arrangement direction of the ink tanks.

FIG. 19 to FIG. 21 show a specific example in which detection of substances is performed using a plurality of sensor units 400 shown in FIG. 18. In this example, a plurality of ink tanks 651 to 654 are detachably attached to an attachment base 655 in an ink jet printer. The ink tanks 651 to 654 contain different color inks and have an exterior of an insulating synthetic resin. A sensor unit 400 supported in a support 610 as shown in FIG. 14 and 15 is provided in the close vicinity of each of the ink tanks 651 to 654. The sensor units 400, namely the supports 610, are integrated with the attachment base 655. Each sensor unit 400 extends in the direction in which the ink in the ink tank increases or decreases (vertical direction).

When a controller incorporated in the ink jet printer constitutes the controller U10 shown in FIG. 18. Using the plurality of sensor units 400, the amounts of inks in the ink tanks 651 to 654 are independently detected. The detection results may be displayed on a display unit (corresponding to the display unit 645 shown in FIG. 18) of the ink jet printer. Each sensor unit 400 does not have to detect the amount of the ink in a continuously variable manner when it is only necessary to warn that the amount of ink is reduced to a predetermined level.

In the case of a personal computer, the display of it can be used as the display unit.

Figure 22:
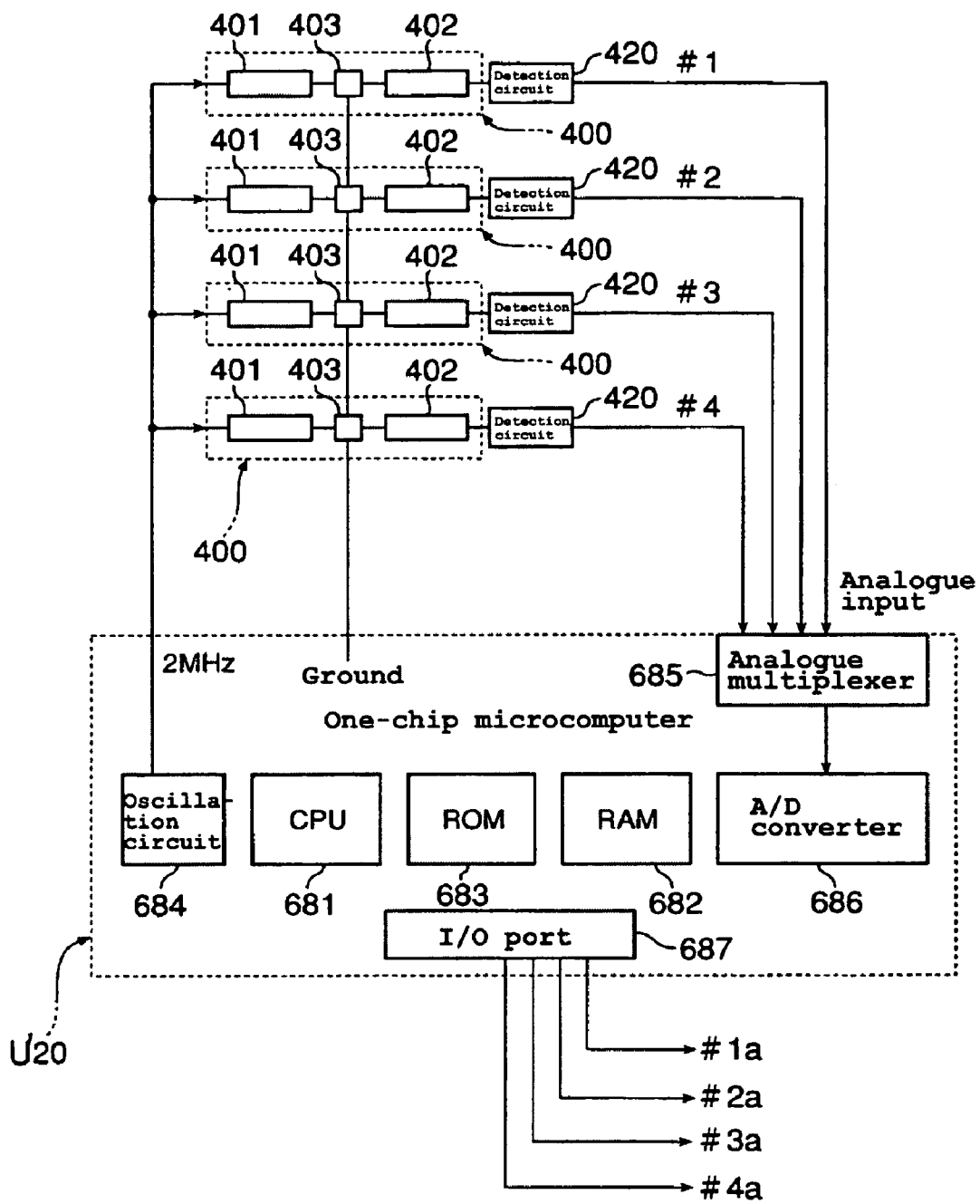
FIG. 22 is a view illustrating an example of a circuit in which outputs from a plurality of sensors are processed in a one-chip microcomputer.

Description of FIG. 22

FIG. 22 shows an example in which outputs from a plurality of sensor units 400 are processed by a one-chip microcomputer. In this embodiment, detection circuits 420 are provided for each of the sensor units 400. The one-chip microcomputer shown in FIG. 22 is incorporated in a printer, for example, and can be used to detect the amounts of inks in a plurality of ink tanks shown in FIG. 19 to FIG. 20 individually.

In FIG. 22, designated as U20 is a one-chip microcomputer (HITACHI H8/3664, for example). The microcomputer U20 has a CPU 681, a RAM 682, a ROM 683, an oscillation circuit 684, an analogue multiplexer 685, an A/D converter 686, and an I/O port 687. The sensor units 400 are connected in parallel to the oscillation circuit 684. Outputs (DC voltages) from the detection circuits 420 are individually inputted into the analogue multiplexer 685. The shielding electrodes 403 are grounded.

In the RAM 682, an OS (operating system) for making the CPU 681 perform a specified operation (control) is stored. In the ROM 683, data which are necessary when the CPU 681 performs the operation are temporarily stored. The oscillation circuit 684 outputs a high-frequency voltage with a specified frequency (2 MHz, for example) using a clock (crystal oscillator). The analogue multiplexer 685 is an analogue switch for selecting one output signal from output signals outputted from the plurality of detection circuits 420. The A/D converter 686 converts an analogue signal from the analogue multiplexer into a digital signal. The I/O port 687 outputs the digital signal produced in the A/D converter 686 to the outside.

The one-chip microcomputer U20 performs the following operation. A high-frequency voltage is outputted from the oscillation circuit 684 to the sensor units 400. Then, each sensor unit 400 outputs a high-frequency voltage according to its electrostatic capacity. The high-frequency voltages from the sensor units 400 are converted into DC voltages by corresponding detection circuits 420 and inputted into the analogue multiplexer 685. The outputs from the detection circuits 420 are designated as #1, #2, #3 and #4, respectively, in FIG. 22.

The analogue multiplexer 685 receives only one output (#1, for example) of the outputs (#1, #2, #3 and #4) from the detection circuits 420 and outputs it to the A/D converter 686. The output from the analogue multiplexer 685 is finally outputted from the I/O port 687 to the outside via the A/D converter 686. In FIG. 22, outputs corresponding to the outputs #1, #2, #3 and #4 from the I/O port 687 are designated as #1a, #2a, #3a and #4a, respectively.

In this embodiment, the analogue multiplexer 685 receives the outputs from the detection circuits 420 in sequence at a specified sampling cycle (for example, receives in the order of #1, #2, #3, #4 in sequence at a specified sampling cycle). In this embodiment, the output from the I/O port 687 is provided when there is an output from the A/I converter 686. Thus, the outputs #1a, #2a, #3a and #4a according to the outputs from the detection circuits 420 are provided in sequence at a specified cycle.

The timing at which the analogue multiplexer 685 receives the outputs from the detection circuits 420 can be arbitrarily set. For example, the reception may be made in response to the operation of a manual switch (not shown) additionally provided. The output from the A/O converter 686 may be temporarily stored in the ROM 683 so that the output from the I/O port 687 can be provided at specified timing or in response to a specified manual operation.

Description of FIG. 23 to FIG. 34

FIG. 23 to FIG. 34 show an example in which the sensor of this invention is used for detection of excrement (stool or urine) in an excrement cup attached to a patient. In the following description, the sensor unit 400 may be shown as sensor S1 or S2.

Figure 23:
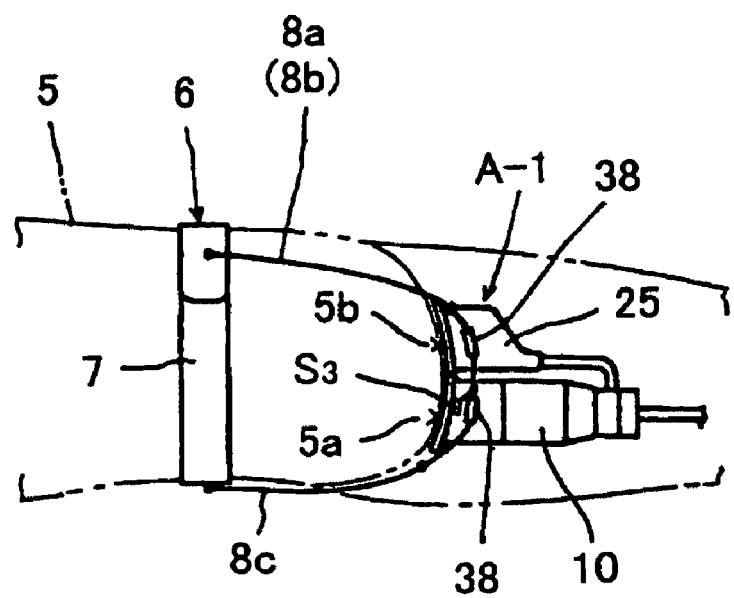
FIG. 23 is a side view illustrating a state where the senor unit is attached to an excrement disposal device.
Figure 24:
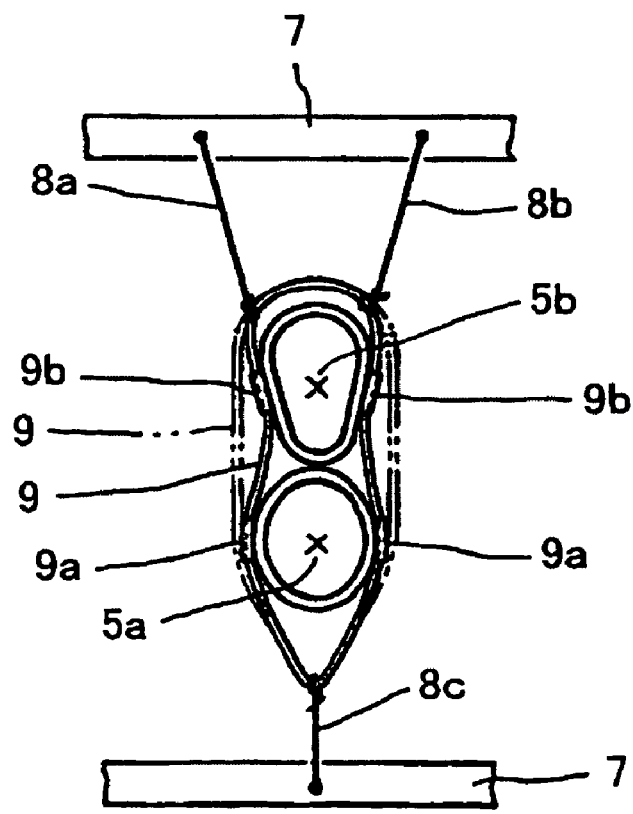
FIG. 24 is a left side view of FIG. 23.
Figure 25:
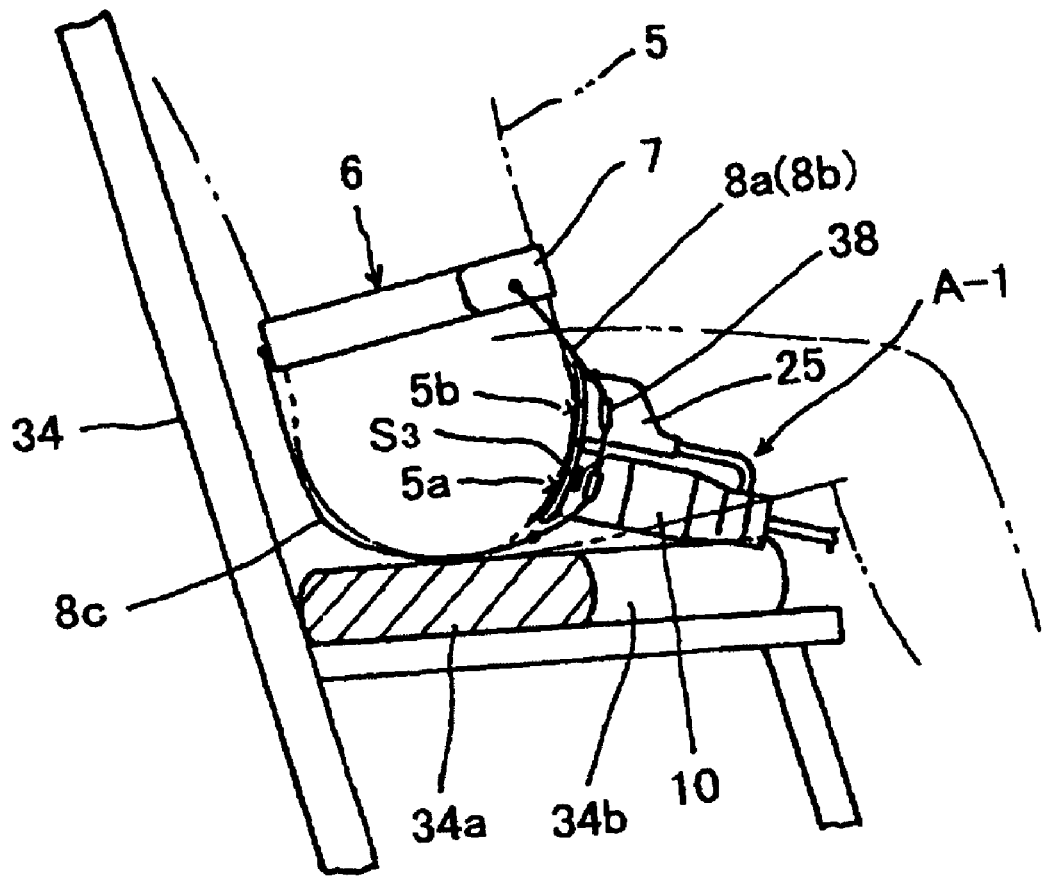
FIG. 25 is a side view illustrating a state where the excrement disposal device is attached to a patient in a sitting position.

In FIG. 23 to FIG. 25, designated as 5 is a wearer, namely a patient, as A-1 is an excrement disposal device. The excrement disposal device A-1 has a stool receiving cup 10 and a urine receiving cup 25 which are separately formed. The cups 10 and 25 are made of a plastic material, for example. The caps 10 and 25 are held in pressure contact with (a part around) the anus 5a and (a part around) the pubic region 5b, respectively, of the patient 5 by a supporter 6.

The supporter 6 has a circumferential belt 7 and a plurality of strings 8a, 8b and 8c. The circumferential belt 7 is wound around the body of the patient 5. Ends of the upper strings 8a and 8b are connected to opposite sides of an upper part of the circumferential belt 7. The lower strings 8c is connected to the middle of a lower part of the circumferential belt 7. A flexible fitting ring 9 is held at three points by ends of the upper strings 8a and 8b and an end of the lower string 8c. As shown in phantom lines in FIG. 24, the fitting ring 9 is deformed into an elliptical shape elongated in a vertical direction and placed in a position surrounding the anus 5a and the pubic region 5b of the patient 5.

The stool receiving cup 10 is placed over the anus 5a of the patient 5. The urine receiving cup 25 has a receiving port which is placed over the pubic region 5b of the patient 5. In this state, both sides of the fitting ring 9 are hooked on hook pieces 9a and 9b attached to both sides of the stool receiving cup 10 and the urine receiving cup 25, respectively, as shown in solid lines in FIG. 24. By the supporter 6, the stool receiving cup 10 and the receiving port of the urine receiving cup 25 are held in pressure contact with (a part around) the anus 5a and (a part around) the pubic region 5b, respectively, of the patient 5.

On both sides of the stool receiving cup 10, attachment sensors S3 for detecting whether the stool receiving cup 10 and the urine receiving cup 25 are properly attached are provided. Each of the attachment sensors S3 comprises a limit switch in this embodiment. The sensors S3 have actuators which are slidably mounted on the upper strings 8a and 8b. The sensors S3 are thereby turned on when the tension of the upper strings 8a and 8b becomes a predetermined value or lower (improper attachment), and turned off when the tension becomes a predetermined value or higher.

To attach the stool receiving cup 10 and the urine receiving cup 25 to a patient 5 in a sitting position, a cushion 34a having a U-shape with an opening at the front as shown in FIG. 25 is placed on the sitting surface of a chair 34. Namely, by seating the patient 5 on the cushion 34a and placing a lower (rear) part of the stool receiving cup 10 in the opening 34b of the cushion 34a, the stool receiving cup 10 can be prevented from contacting the sitting surface of the chair 34.

The stool receiving cup 10 and the urine receiving cup 25 are constituted as shown in FIG. 26 to FIG. 31. The stool receiving cup 10 is formed in a cylindrical shape elongated in a longitudinal direction as a whole. Namely, the stool receiving cup 10 has a width which is smaller than the vertical length thereof and is elongated in the longitudinal direction. The stool receiving cup 10 has a cylindrical shape with a length of about 112 mm, a height of about 50 mm, and a width of about 40 mm. The stool receiving cup 10 is partitioned into front and rear (right and left in FIG. 26) sections by a partition 11 located at a longitudinal intermediate part therein. Namely, in the stool receiving cup 10, a stool chamber 12 and an auxiliary machine chamber 14 are formed on the front side and the rear side, respectively, of the partition 11. The front side (left side in FIG. 26) of the stool chamber 12 opens to the outside (front) as a stool receiving port 12a. A ring-shaped sealing member 13 of a soft rubber or resin is attached on the edge of the receiving port 12a so that the receiving port 12a can be in close contact with the part around the anus 5a. The stool chamber 12 and the auxiliary machine chamber 14 must be as water-tight as possible.

The partition 11 is made of a hard plastic material with high strength. A discharge pipe 16 extends in the longitudinal direction and is rotatably supported by the partition 11. The discharge pipe 16 has a front end exposed in the stool chamber 12. A first nozzle 15 (stool pulverizer) for injecting washing water (washing liquid) is located in the stool chamber 12 and attached to the front end of the discharge pipe 16. The first nozzle 15 is set to inject the washing liquid in a direction perpendicular to the axis of the discharge pipe 16.

A motor (a ultrasonic motor in this embodiment) M is attached on the side of the auxiliary chamber 14 of the partition 11. The motor M is used to rotate the discharge pipe 16. The motor M has a ring shape and the discharge pipe 16 extends through the hollow of the motor M. The motor M is rotatably driven by signals from a terminal circuit board 60 housed in the auxiliary machine chamber 14. Namely, to pulverize stool in the stool chamber 12, the first nozzle 15 is oriented downward and the discharge pipe 16 is rotated forward and backward so that the first nozzle 15 can be swung through an angle of 90° to the right and left from a vertical line for a predetermined period of time (about 20 seconds in this embodiment). When pulverizing of the stool is completed, the discharge pipe 16 is rotated in one direction for a predetermined period of time (ten seconds in this embodiment) so that the first nozzle can be rotated through 360° to wash the anus 5a and the inside of the stool cup 10.

The discharge pipe 16 is rotatably connected to a supply pipe 18 provided in the auxiliary machine chamber 14 via a rotary joint 17. The supply pipe 18 is connected to a hereinafter described washing water supply unit 40 via a supply passage 20a formed through a rear wall 20 of the auxiliary machine chamber 14 and a supply passage 21a formed through a rear joint 21. Water (warm water) supplied from the washing water supply unit 40 is injected from the first nozzle 15 into the stool chamber 12. The stool excreted in the stool chamber 12 is pulverized and the anus 5a of the patient 5 is washed by the washing water.

The first nozzle 15 injects washing water in a shape of a sector having an angle α of about 110° and a width of about 1 mm. A stool discharge pipe 23 is provided at a lower part in the auxiliary machine chamber 14. The stool discharge pipe 23 has a front end which is connected to a lower rear part of the stool chamber 12 and opens in the stool chamber 12, and a rear end which is connected to a hereinafter described stool discharge unit 45 via a stool discharge passage 20b formed through the rear wall 20 of the auxiliary machine chamber 14 and a stool discharge passage 21b formed through the rear joint 21. By the stool discharge unit 45, the stool pulverized in the stool chamber 12 is sucked and removed (discharged) to the outside.

Figure 26:
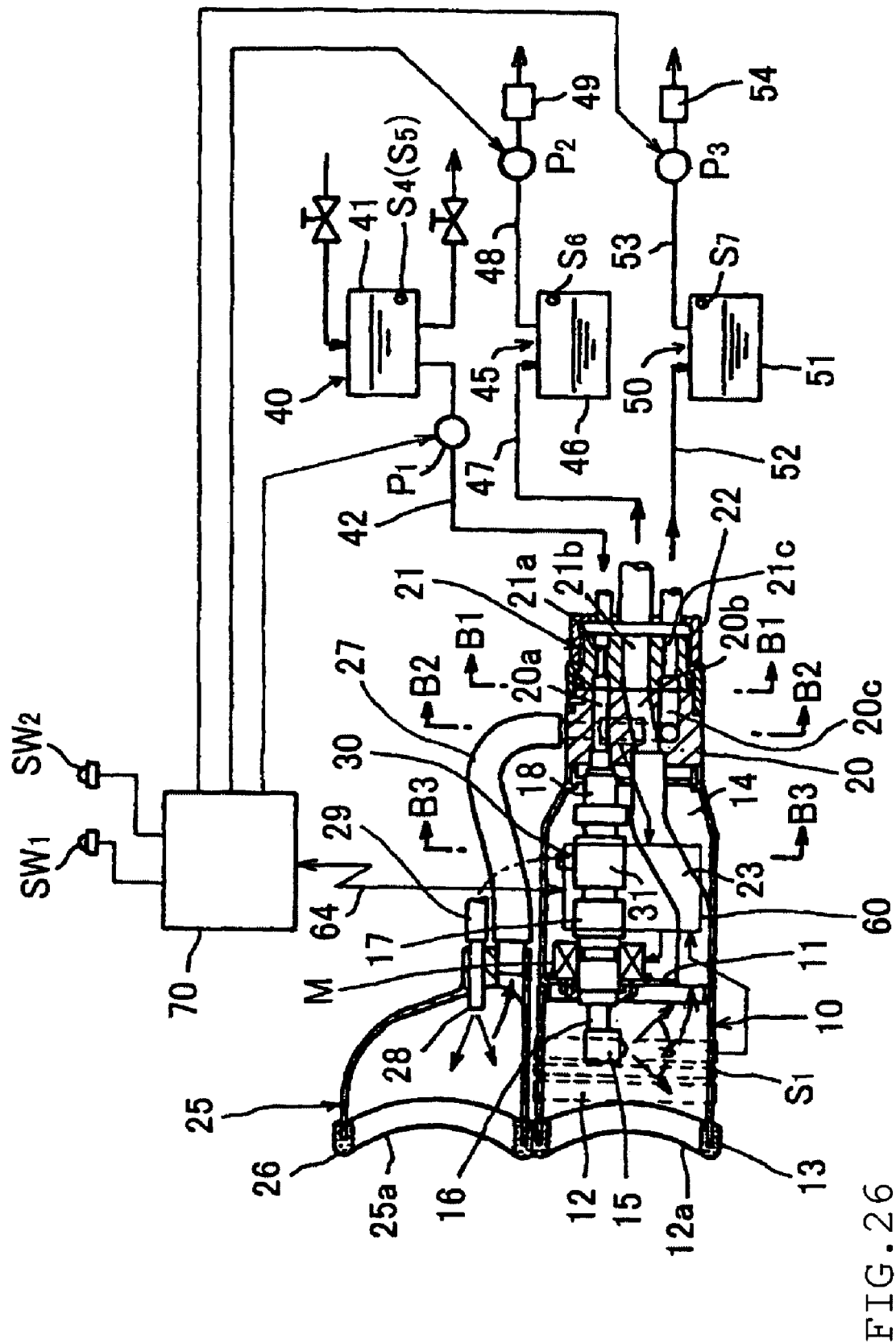
FIG. 26 is a cross-sectional side view of an essential part of the excrement disposal device.
Figure 27:
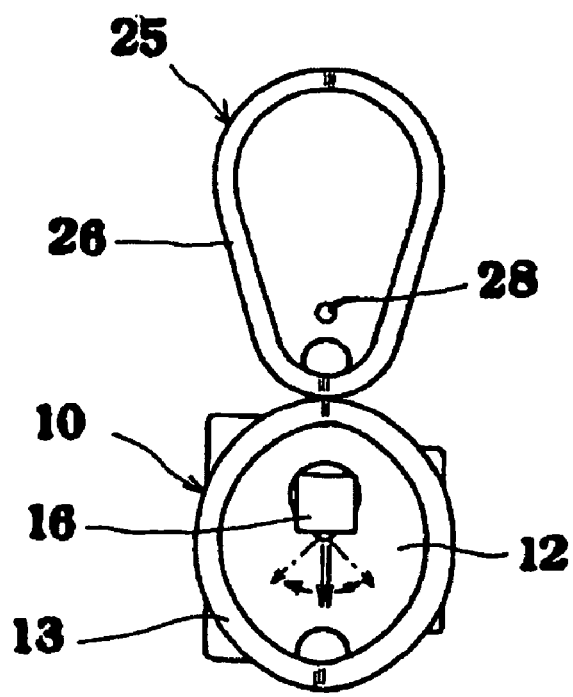
FIG. 27 is a left side view of FIG. 26.
Figure 28:
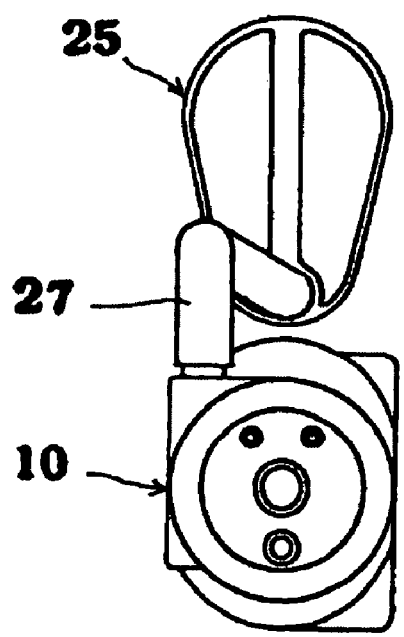
FIG. 28 is a right side view of FIG. 26.

The urine receiving cup 25 has a receiving port which is open at the front as shown in FIGS. 26 and 27. The urine receiving cup 25 is formed in a conical shape with an upper surface which inclined downward toward the rear. The urine receiving cup 25 has a length of about 52 mm, a height of about 55 mm, and a width of about 36 mm.

The urine receiving cup 25 has a receiving port 25a having an elliptical shape elongated in a vertical direction at the front. A sealing member 26 of a soft rubber or resin is attached on the edge of the receiving port 25a so that the receiving port 25a can be in close contact with the area around the pubic region 5b. A urine discharge hose 27 is connected to a lower rear part of the urine receiving cup 25. The urine discharge hose 27 has a diameter of about 10 mm. The urine discharge hose 27 has a rear end connected to an upper part of a urine discharge passage 20c formed through the rear wall 20 of the auxiliary chamber 14. Namely, the urine discharge hose 27 is connected to a hereinafter described urine discharge unit 50 via the urine discharge passage 20c and a urine discharge passage 21c formed through the rear joint 21. By the urine discharge unit 50, the urine excreted in the urine receiving cup 25 is sucked and removed to the outside.

To provide a function of washing the pubic region 5b of the patient 5, a second nozzle 28 is attached at a rear part in the urine receiving cup 25. The second nozzle 28 is connected to a mid-portion of the supply pipe 18 via a second discharge hose 29, an electromagnetic valve 30 and a branch connection 31. By opening the electromagnetic valve 30 when the patient 5 finishes urinating, washing water (hot water) supplied from the washing water supply unit 40 is injected to the pubic region 5b of the patient 5 from the second nozzle 28. In this case, the washing water is injected from the second nozzle 28 at an angle of, for example, 40°.

Figure 29:
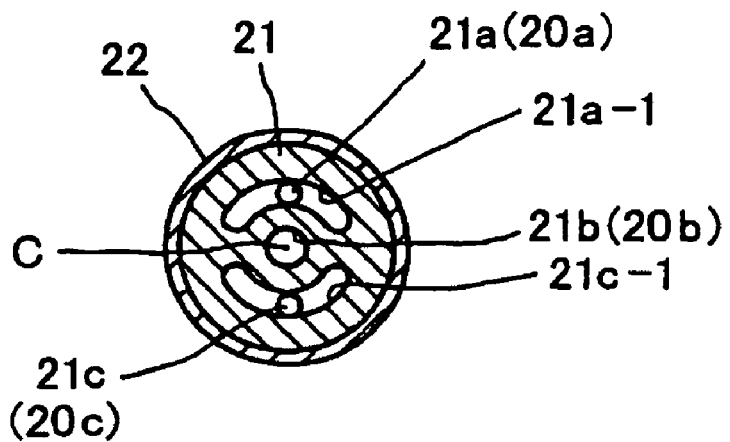
FIG. 29 is a cross-sectional view taken along the line B1-B1 in FIG. 26.

As shown in FIG. 26 and FIG. 29, the stool discharge passages 20b and 21b are faced to each other at the axis C of the rear joint 21. The supply passages 20a and 21a are faced to each other in a position offset from the axis C. The urine discharge passages 20c and 21c are faced to each other in a position offset from the axis C. As shown in FIG. 7, the position where the supply passages 20a and 21a are faced to each other and the position where the urine discharge passages 20c and 21c are faced to each other are vertically symmetric with respect to the axis C. At the facing parts of the supply passage 21a and the urine discharge passage 21c in the rear joint 21, slots 21a-1 and 21c-1 (which serve as connection passages) having a shape of a 120 degree arc about the axis C.

The rear joint 21 is connected to the rear wall 20 via a cylindrical coupler 22. The rear joint 21 is rotatable through an angle of about 120° around its axis so that the rear joint 21 can be rotated relative to the rear wall 20 when the patient 5 rolls to the right or left and the stool receiving cup 10 and the urine receiving cup 25 are rotated to the right or the left. Namely, the hoses of the washing water supply device 40, the stool discharge unit 45 and the urine discharge unit 50 can be prevented from being twisted.

Figure 30:
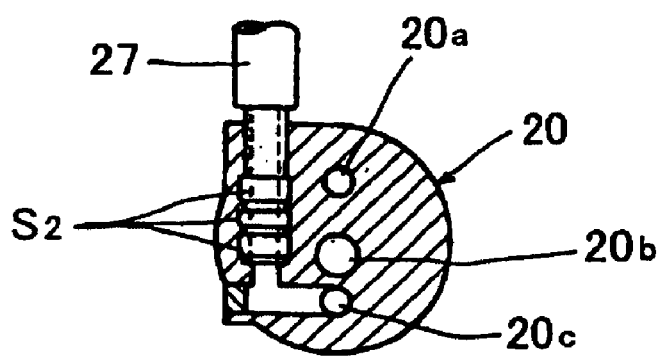
FIG. 30 is a cross-sectional view taken along the line B2-B2 in FIG. 26.
Figure 31:
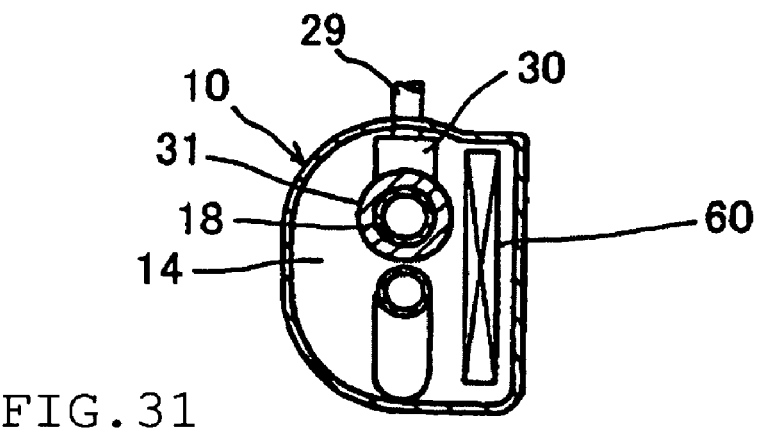
FIG. 31 is a cross-sectional view taken along the line B3-B3 in FIG. 26.
Figure 32:
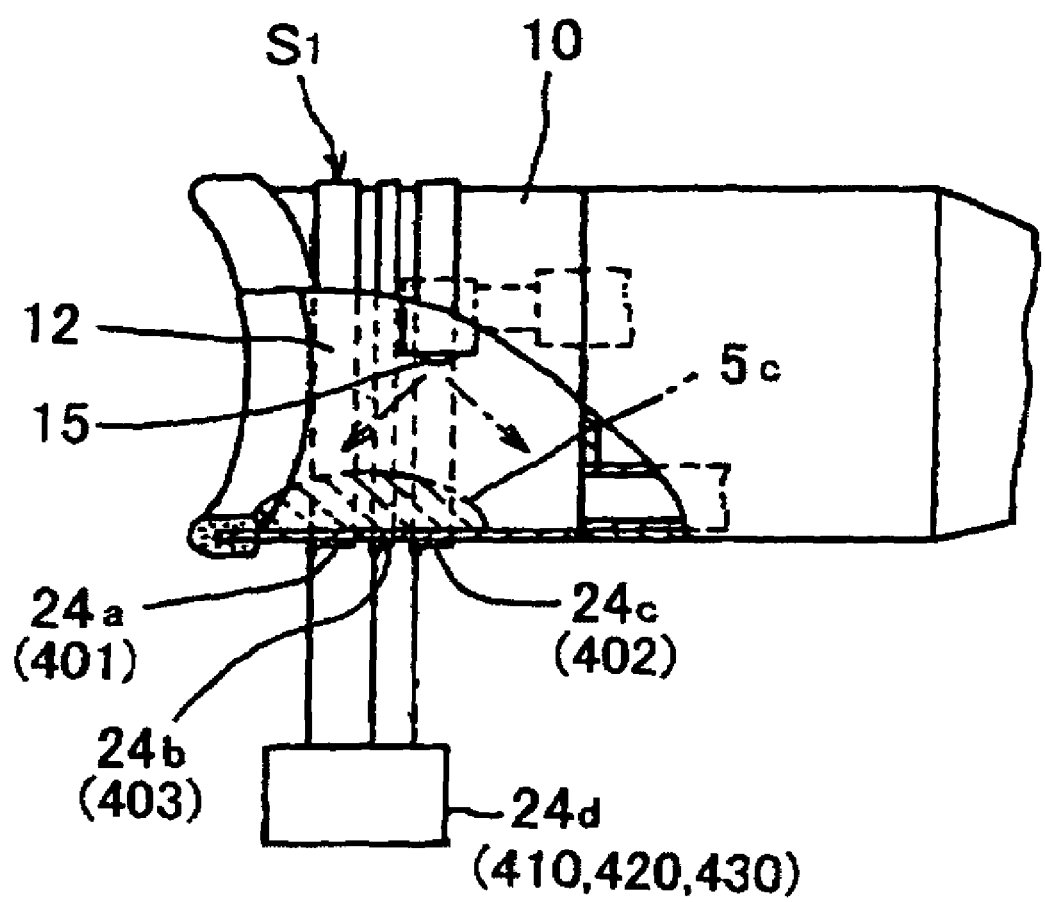
FIG. 32 is a circuit diagram of a stool sensor.

A stool sensor S1 is attached on the outer periphery of the stool chamber 12 (FIG. 26). A urine sensor S2 is attached on the outer periphery of an upright portion of the urine discharge passage 20c (FIG. 30). Detection signals from the stool sensor S1 and the urine sensor S2 (each of which corresponds to the sensor unit 400) are transmitted to the terminal circuit board 60 described previously. The stool sensor S1 and the urine sensor S2 are electrostatic capacity sensors of the same type.

The stool sensor S1 (the urine sensor S2) corresponds to the sensor unit 400 described previously. Thus, the outer peripheral wall of the stool chamber 12, namely the stool receiving cup 10 is made of an insulating material such as a plastic. Ring-shaped transmission electrode 24a (corresponding to 401), protection electrode 24b (corresponding to 403), and a reception electrode 24c (corresponding to 402) are wound around the outer periphery of the stool chamber 12 at specified longitudinal intervals. The transmission electrode 24a, protection electrode 24b and the reception electrode 24c are connected to a detecting circuit 24d (which corresponds to the circuit except the electrodes shown in FIG. 1).

The electrostatic capacity between the transmission electrode 24a and the reception electrode 24c varies depending upon whether there is stool between them. Thus, by detecting the variation of the electrostatic capacity with the detecting circuit 24d, it can be determined whether there exists stool in the stool receiving cup 10.

The washing water supply unit 40 is for supplying water or water mixed with an antiseptic or a liquid soap as washing liquid (washing water). As shown in FIG. 26, the washing water supply unit 40 has a warm water tank 41 for adjusting the washing water to a predetermined temperature. The warm water (washing water) in the warm water tank 41 is supplied to the stool receiving cup 10 through a warm water pump P1 and a supply hose 42. A high-temperature sensor S4 and a low-temperature sensor S5 are provided in the warm water tank 41. The high-temperature sensor S4 is turned on when the temperature becomes, for example, 42° C. or higher. The low-temperature sensor S5 is turned on when the temperature becomes, for example, 25° C. or lower. When the sensor S4 or S5 is turned on, the warm water pump P1 is stopped. When the stool sensor S1 or the urine sensor S2 is actuated when the sensors S4 and S5 are off, the warm water pump P1 is activated and washing water is injected from the first nozzle 15 or the second nozzle 28 (to wash the anus 5a or the pubic region 5b of the patient 5).

The stool discharge unit 45 described previously has a sealed stool tank 46 as shown in FIG. 26. An upper part of the stool tank 46 is detachably connected to the stool discharge passage 21b via a stool discharge hose 47 (with a diameter of, for example, about 10 mm). An upper part of the stool tank 46 is connected to (a suction port of) a stool suction pump P2 via a suction hose 48. The stool suction pump P2 has a discharge pipe to which a catalyst (deodorizer) 49 is connected. The stool suction pump P2 is activated when the stool sensor S1 is actuated and establishes a negative pressure within the stool tank 46 so that stool having flown down to a lower part of the stool chamber 12 can be sucked into the stool tank 46. Gas in the stool tank 46 sucked by the stool suction pump P2 is purified by the catalyst 49 and discharged into the outside air. The stool tank 46 is provided with a fullness sensor S6 for detecting the fullness of the stool tank 46.

The urine discharge unit 50 has a sealed urine tank 51 as shown in FIG. 26. An upper part of the urine tank 51 is connected to the urine discharge passage 21c via a urine discharge hose 52. An upper part of the urine tank 51 is connected to (a suction port of) a urine suction pump P3 via a suction hose 53. The urine suction pump P3 has a discharge pipe to which a catalyst (deodorizer) 54 is connected. The urine suction pump P3 is activated when the urine sensor S2 is actuated and establishes a negative pressure within the urine tank 51 so that urine having flown down to a lower part of the urine receiving cup 25 can be sucked into the urine tank 51. Gas in the urine tank 51 sucked by the urine suction pump P3 is purified by the catalyst 54 and discharged into the outside air. The urine tank 51 is provided a fullness sensor S7 for detecting the fullness of the urine tank 51.

Figure 33:
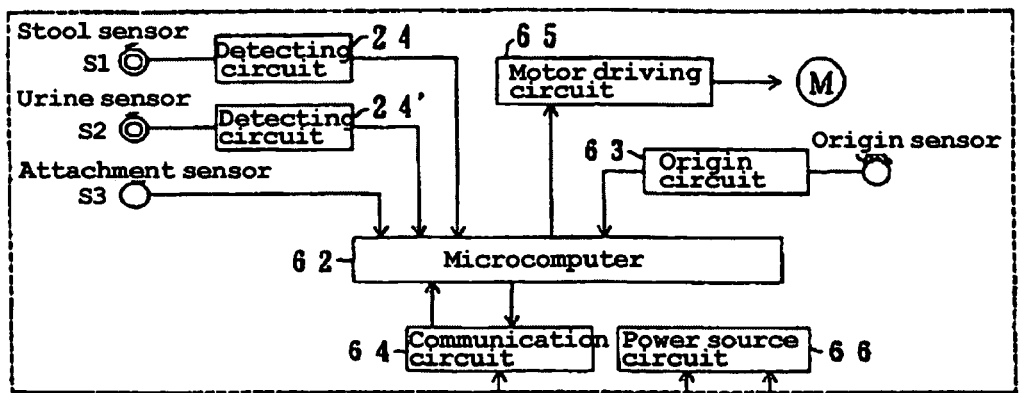
FIG. 33 is a block diagram of a control unit of the excrement disposal device.
Figure 33:
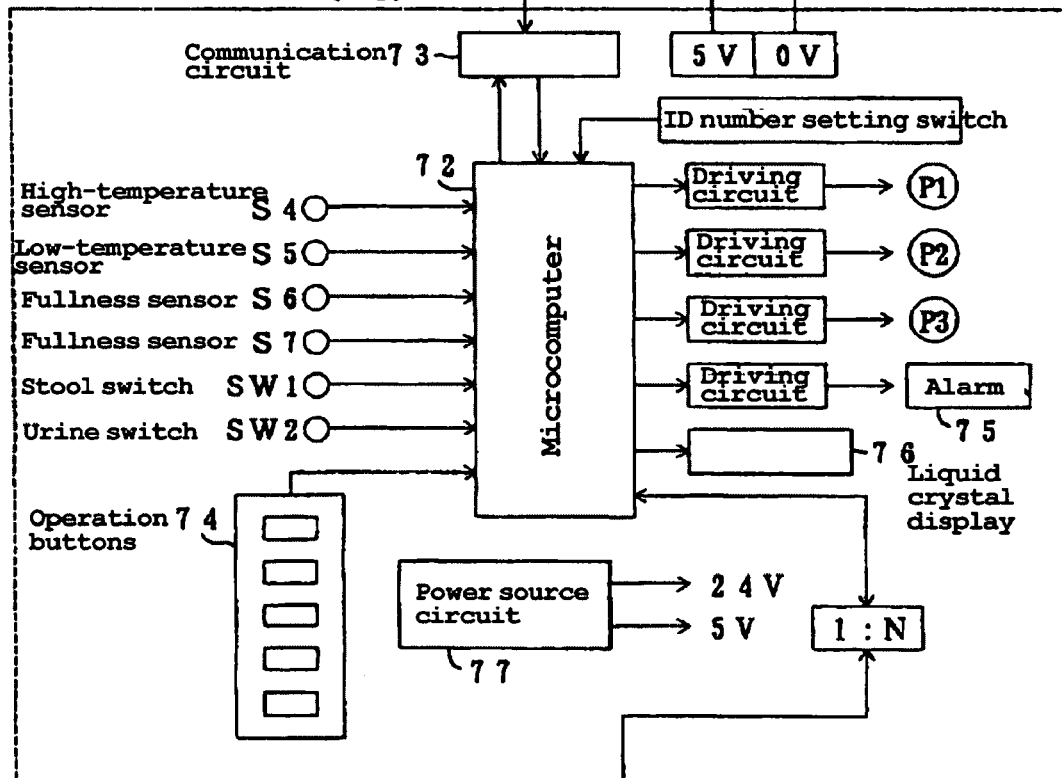
Figure 33:
Figure 34:
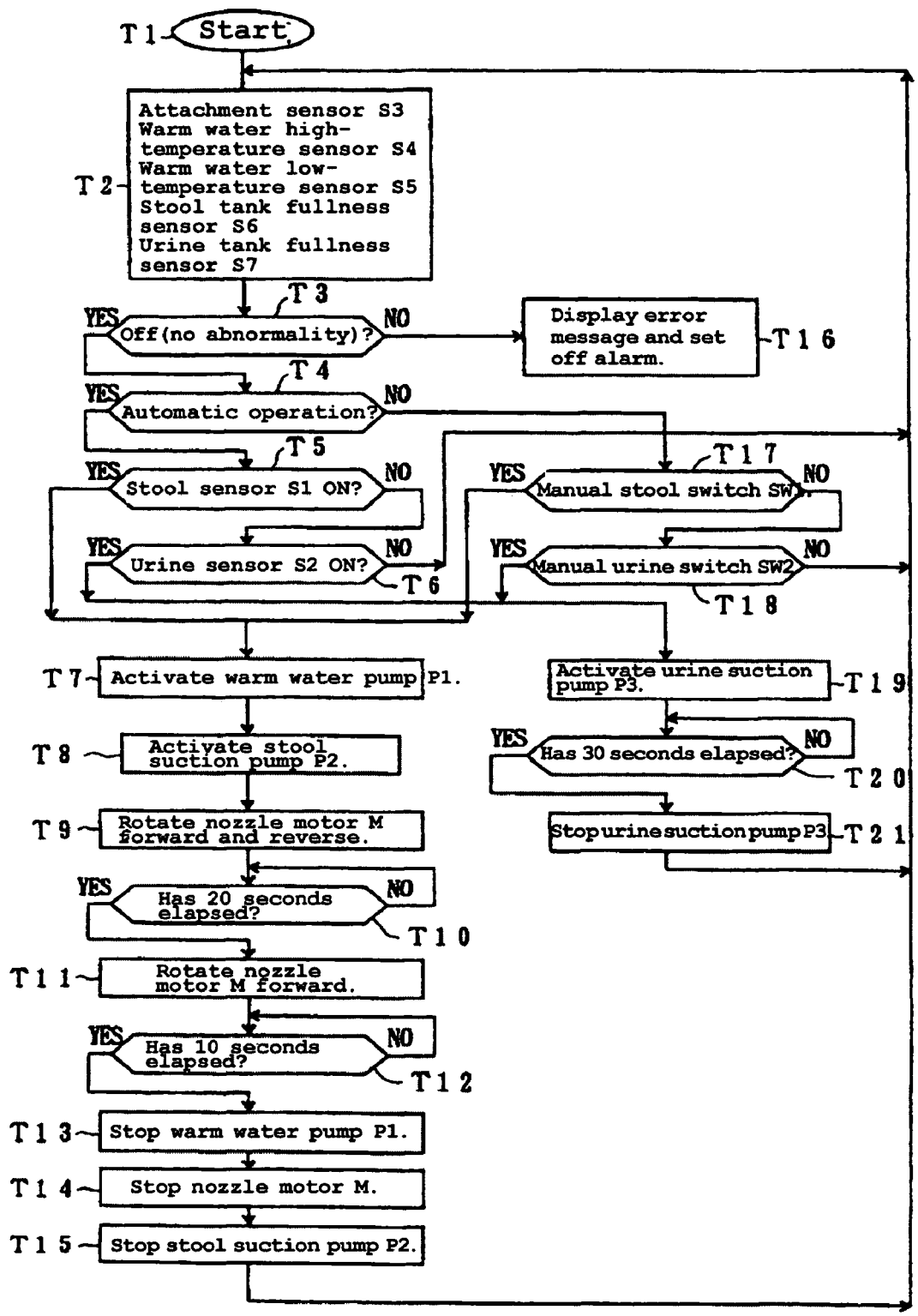
FIG. 34 is a flowchart of the control unit.

In FIG. 26, designated as 70 is an external controller for applying a specified power source voltage to the terminal circuit board 60 described previously. The controller 70 communicates with the terminal circuit board 60 through a communication line 64 to control each equipment. FIG. 33 is a block diagram of the terminal circuit board 60 and a control unit incorporated in the controller 70, FIG. 34 is a flowchart of the control unit. In FIG. 34, designated as 61 is an attachment control unit incorporated in the terminal circuit board 60, as 71 is an external control unit incorporated in the controller 70. The attachment control unit 61 has a terminal microcomputer 62. Data from the stool sensor S1 and the urine sensor S2 are inputted into the terminal microcomputer 62 via detecting circuits 24 and 24', respectively. A signal from the attachment sensor S3 is also inputted into the terminal microcomputer 62. Further, data from an origin sensor S8 for detecting the original position of the first nozzle 15 are also inputted into the microcomputer 62 via an origin circuit 63. The microcomputer 62 transmits the data and signal to the external control unit 71 of the controller 70 via the communication circuit 64, and receives data processed in the external control unit 71 to control the motor M via a motor driving circuit 65. Designated as 66 is a power source circuit for supplying power from the controller 70 side to the terminal circuit board 60.

The external control unit 71 of the controller 70 has a host microcomputer 72, into which the data and signal from the terminal microcomputer 62 are inputted via communication circuit 73. Signals from the high-temperature sensor S4, the low-temperature sensor S5, the fullness sensors S6 and S7, a manual stool switch SW1, a manual urine switch SW2 and so on are also inputted into the microcomputer 72. Further, the driving time and the forward and reverse rotation angles of the motor M, set values of the sensors and so on are inputted into the microcomputer 72 through operation buttons 74. The host microcomputer 72 stores and arithmetically processes the inputted data and signals and outputs specified command signals to the terminal microcomputer 62, and controls the warm water pump P1, the stool suction pump P2 and the urine suction pump P3 via driving circuits. In abnormal situations, the microcomputer 72 actuates an alarm 75 or displays a necessary indication on a liquid crystal display 76. When necessary, the data in the controller 70 are transmitted to a personal computer 78 installed in a central control room via a communication line and stored and centrally managed therein. Designated as 77 is a power source circuit of the controller 70.

The operation of the attachment control unit 61 and the external control unit 71 will be described with reference to the flowchart in FIG. 34. In FIG. 34, T1 to T21 represents the steps of the flowchart. When the control program is stared in step T1, signals from the attachment sensor S3, the high-temperature sensor S4, the low-temperature sensor S5, the fullness sensor S6 of the stool tank 46 and the fullness sensor S7 of the urine tank 51 are inputted in step T2. In step T3, it is determined whether there is an abnormality in each sensor. When an abnormality is found in step T3, the program goes to step T16 to display an error message and set off an alarm. When there is no abnormality (the signals are off), the program goes to step T4. In step T4, it is determined whether the device is in automatic operation or not.

In the case of automatic operation, it is determined whether the stool sensor S1 is on or not in step T5. When the stool sensor S1 is on, the program performs steps T7 to T10 to activate the warm water pump P1 and the stool suction pump P2 and rotates the motor M forward and reverse for about 20 seconds. Then, warm water is injected from the first nozzle 15 and the first nozzle 15 is swung through about 90° to the right and left from a vertical line. Stool 5c accumulated at the bottom of the stool receiving cup 10 is thereby pulverized. The thus pulverized stool 5c is sucked and discharged through the stool discharge pipe 23, the stool discharge passages 20b and 21b and the stool discharge hose 47 and received in the stool tank 46.

After having been rotated in forward and reverse for 20 seconds, the motor M is rotated in one direction for about 10 seconds in steps T11 and T12. Then, the first nozzle 15 injects washing water via the discharge pipe 16 while being rotated about a longitudinal line to wash the entire inside of the stool receiving cup 10 and the anus 5a of the patient 5. Then, the program performs steps T13 to T15 to stop the warm water pump 13, the motor M, and the stool suction pump P2, and then jumps to step T2.

When the stool sensor S1 is off in step T5, it is determined whether the urine sensor S2 is on in step T6. When the urine sensor S2 is off, the program jumps to step T2. When the urine sensor S2 is on, the program performs steps T19 to T21 to activate the urine suction pump P2 for 30 seconds. The urine excreted into the urine cup 25 is thereby sucked and received in the urine tank 51. After stopping the urine suction pump P2 in step T21, the program jumps to step T2.

When the device is not in automatic operation, namely, in manual operation, in step T4, it is determined whether the manual stool switch SW1 is on in step T17. When the manual stool switch SW1 is on, the program performs steps T7 to T15 whereas when the manual stool switch SW1 is off, the program goes to step T18. In step T18, it is determined whether the manual urine switch SW2 is on. When the manual urine switch SW2 is on, the program performs steps T19 to T21 whereas when the manual urine switch SW2 is off, the program jumps to step T2. When the pubic region 5b of the patient 5 is washed after urination, the electromagnetic valve 30 shown in FIG. 4 is opened and the warm water pump P1 is activated before the urine suction pump P3 is stopped in step T21 so that the washing water can be injected from the second nozzle 28 to the pubic region 5b of the patient 5.

Figure 35:
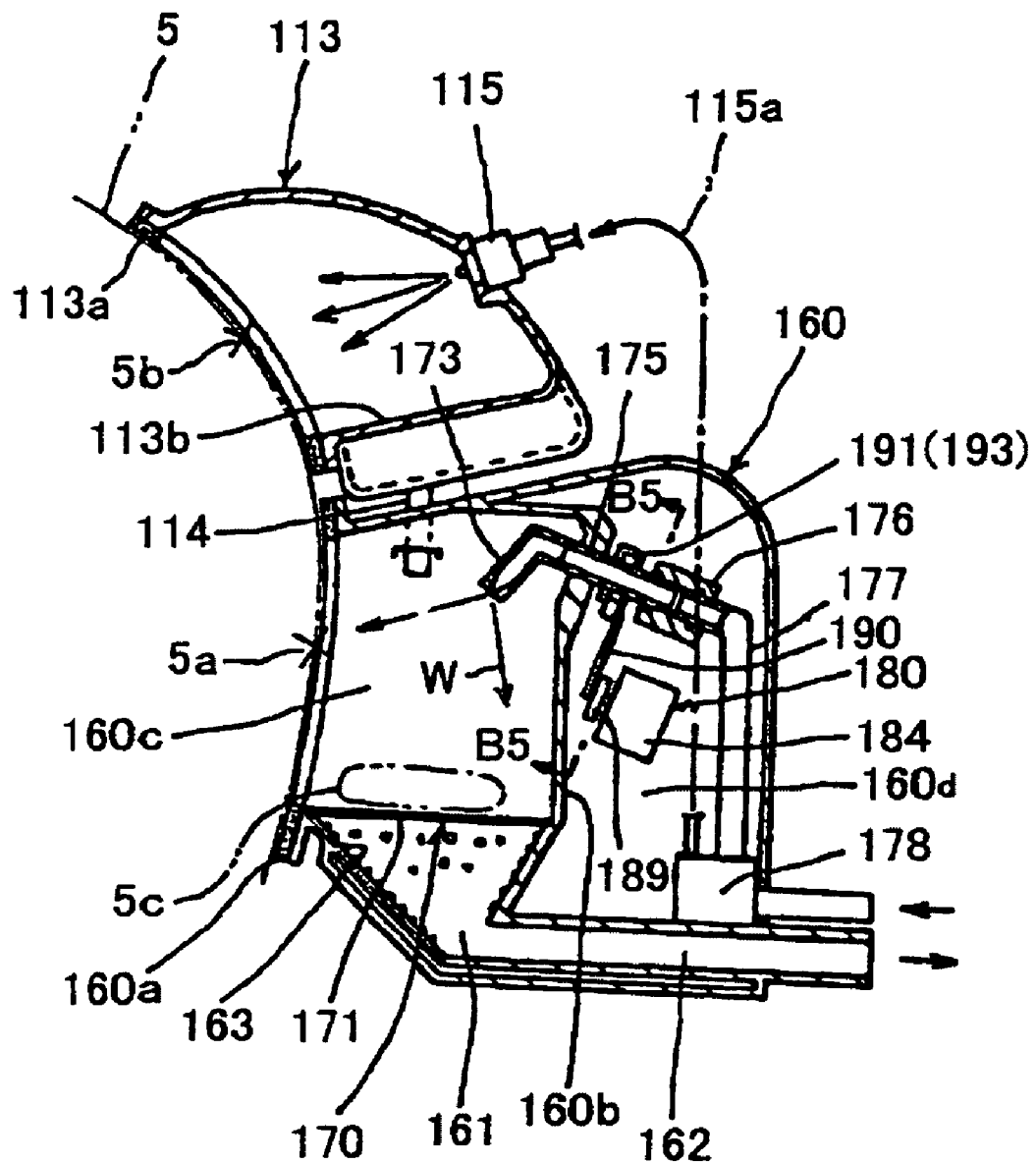
FIG. 35 is a cross-sectional side view illustrating another example in which a sensor unit is provided in an excrement cup.
Figure 36:
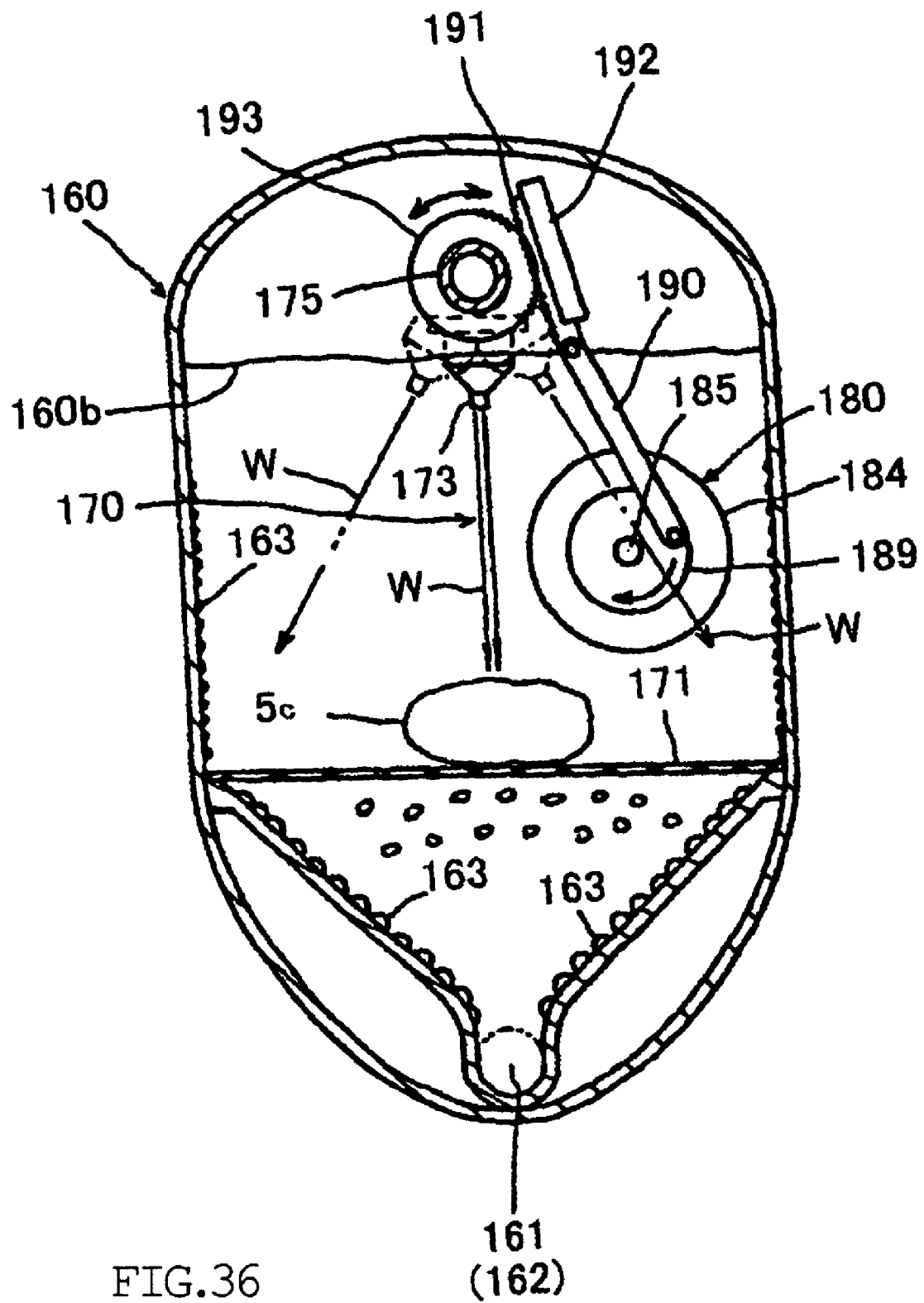
FIG. 36 is a cross-sectional view taken along the line B5-B5 in FIG. 35.

Description of FIG. 35 and FIG. 36

FIG. 35 and FIG. 36 show another example in which a capacitance-coupled sensor is provided in an excrement cup. In this example, the sensor unit 400B as shown in FIG. 6 or the sensor unit 400C as shown in FIG. 9 is provided in the excrement cup. In FIG. 35 and FIG. 36, a sensor unit corresponding to the sensor unit 400B or 400C is referred to as "net" and designated as 171.

An excrement disposal device A-3 has a stool receiving cup 160 and a urine receiving cup 113 which are formed of a plastic material separately. As shown in FIG. 35, the stool receiving cup 160 is partitioned into front and rear sections by a partition 160b. Namely, in the stool receiving cup 126, a stool chamber 160c for receiving stool and an auxiliary machine chamber 160d for housing auxiliary machines are formed at the front and rear, respectively. The stool chamber 160c has a lower part which is tapered downward like a funnel with a discharge port 161 at the bottom. The discharge port 161 is communicated from the lower rear end of the stool receiving cup 160 to the outside via a stool discharge passage 162 formed at the bottom of the stool receiving cup 160. A multiplicity of projections 163 are formed over almost the entire inner surfaces of the stool chamber 160c to prevent adhesion of stool.

A stool pulverizer 170 is provided in the stool chamber 160c. Namely, a net (net member) 171 with a specified mesh size (5 mm in this embodiment) is strung across a lower part in the auxiliary machine chamber 160d (the sensor unit 400C as shown in FIG. 9 or the sensor unit 400B as shown in FIG. 6 may be used). The net 171 is placed over the discharge port 161. Namely, the net 171 is placed between the stool receiving port and the discharge port 161 so that stool excreted into the stool receiving cup 160 cannot move down into the discharge port 161 without passing through the net 171. A first nozzle 173 for injecting washing water (water or warm water) W is provided at an upper part in the stool chamber 160c. A discharge pipe 175 extends through the partition 160b and rotatably supported thereby. The discharge pipe 175 has a front end to which the first nozzle 173 is attached. The discharge pipe 175 is rotatably connected to a first introduction pipe 177 via a pipe joint 176. The first introduction pipe 177 is connected to a washing water supply unit via a relay 178.

The first nozzle 173 injects washing water to the upper surface of the net 171. Part of the washing water is also injected to the anus 5a of the patient 5. Namely, the washing water is injected into a shape which is so broad in the longitudinal direction as to extend from a rear part of the net 171 to the anus 5a of the patient 5 as shown in FIG. 36, and narrow (linear) in the lateral direction as shown in FIG. 35.

The first nozzle 173 is swung to the right and left via the discharge pipe 175 by a nozzle driving unit 180 housed in the auxiliary machine chamber 160d. As shown in FIG. 35, the nozzle driving unit 180 has an electric motor (driving unit) 184 having an output shaft 185 to which a connecting rod 190 is connected via a crank web 189. The connecting rod 190 has an end connected to a rack 191 slidably attached to a rack holder 192. The rack 191 is in meshing engagement with a pinion gear 193 attached to a rear part of the discharge pipe 175.

The rotation of the electric motor 184 is converted into linear reciprocating motion by the crank web 189 and the connecting rod 190, and the rack 191 is reciprocated up and down. Namely, by the reciprocating motion of the rack 191, the first nozzle 173 is swung to the right and left through a specified angle via the pinion gear 193 and the discharge pipe 175. The washing water W injected from the first nozzle 173 is moved to the right and left as shown in FIG. 35 to pulverize stool (shits) 5d on the net 171. The pulverized stool flows down to the discharge port 161 through the net 171.

The stool discharge passage 162 is connected to a stool discharge unit, by which the stool pulverized by the stool pulverizer 170, urine having flown down from the urine receiving cup 113 into the stool chamber 160c, water injected from the first and second nozzles 173 and 115 and used and so on are sucked through the stool discharge passage 162 and discharged to the outside.

Figure 37:
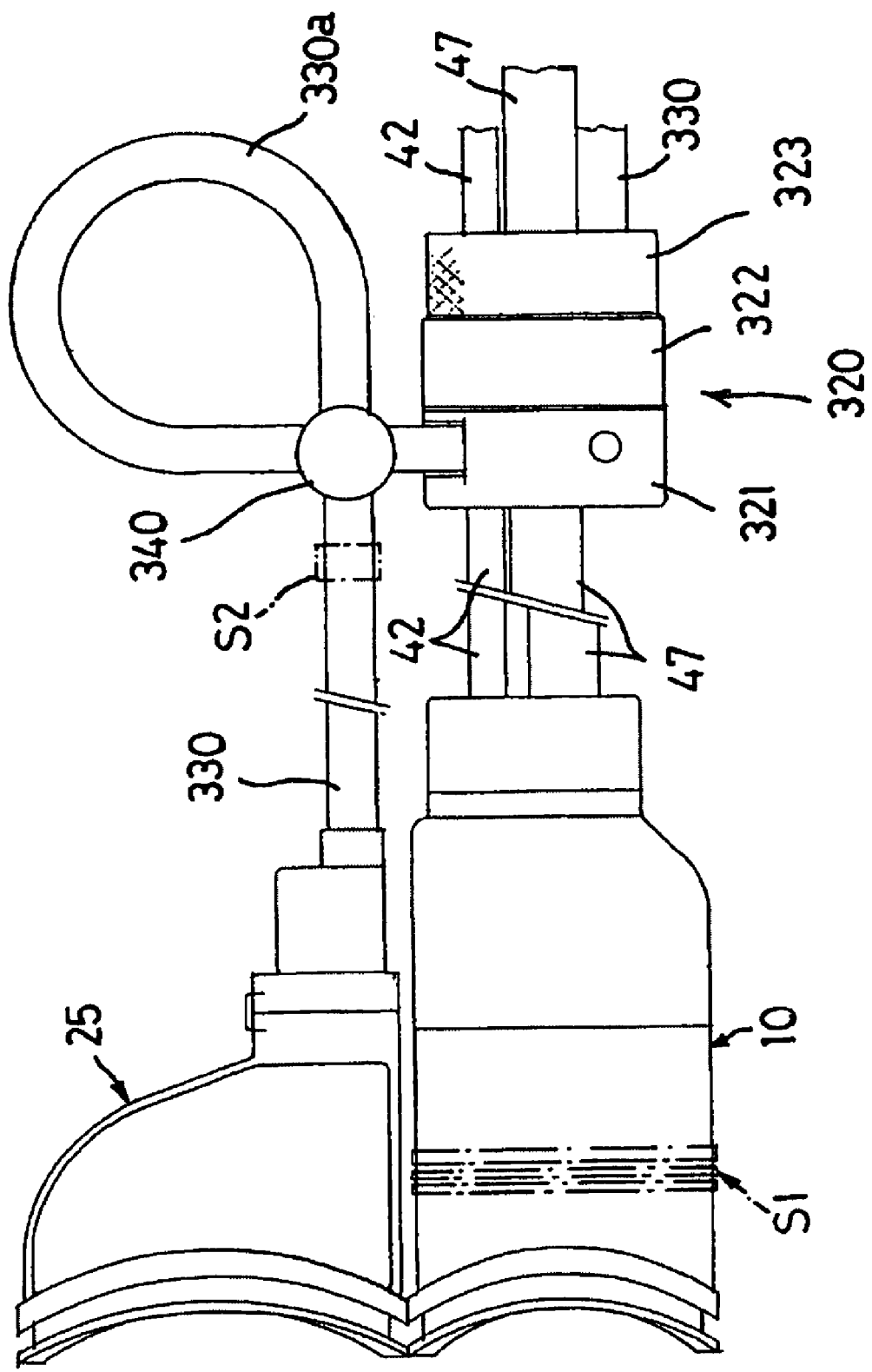
FIG. 37 is a side view illustrating another example in which a sensor unit is provided in relation to the excrement cup.
Figure 38:
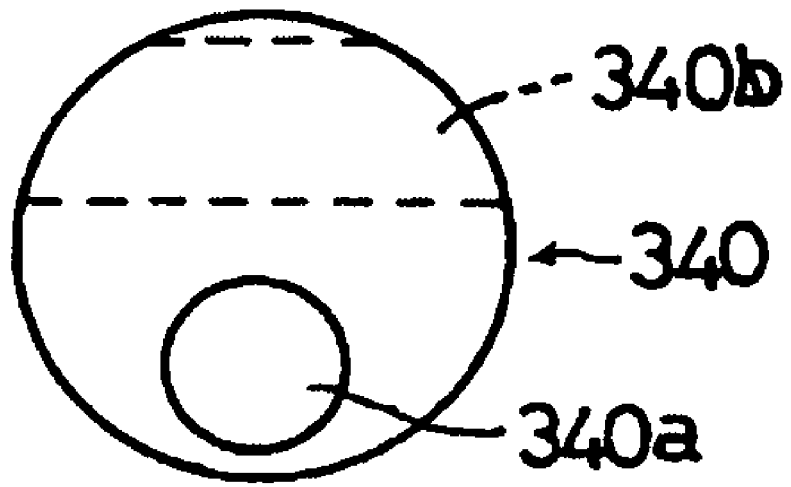
FIG. 38 is a top plan view of a holding clip shown in FIG. 37.
Figure 39:
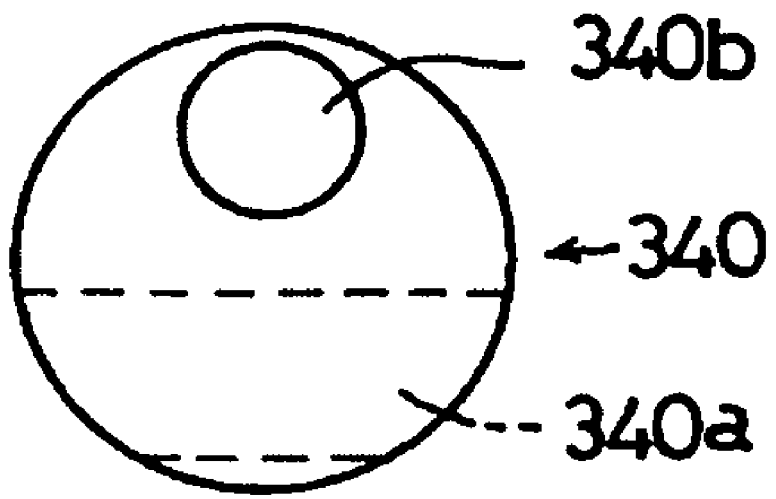
FIG. 39 is a right side view of FIG. 38.

Description of FIG. 37 to FIG. 39

FIG. 37 to FIG. 39 show an example of an arrangement of a urine discharge hose and a rotary joint which is suitable when a stool receiving cup and a urine receiving cup are formed as separate pieces detachable from each other. A stool receiving cup 10 and a urine receiving cup 25 as shown in FIG. 26 are used. In this example, the rotary joint 320 is provided outside and in the vicinity of the stool receiving cup 10. The rotary joint 320 has the same function as the joint 21 shown in FIG. 26 but different from it in that it is located outside the stool receiving cup 10. Namely, the rotary joint 320 has a first member 321, a second member 322 rotatably connected to the first member 321, and a coupler 323 for connecting hoses and so on to the second member 322. The rotary joint 320 is connected to a mid-portion of a stool discharge hose 47 and a washing liquid supplying hose 42 for the stool receiving cup in the vicinity of the stool receiving cup 10. Thus, the rotary joint 320 can be externally attached to the stool receiving cup 10, and twist of hoses 47 and 42 can be prevented from affecting the wearer.

A urine discharge hose 330 (corresponding to the urine discharge hose 27 in FIG. 26) extending from the urine receiving cup 25 is connected to a urine tank via the rotary joint 320. The part of the urine discharge hose 330 between the urine receiving cup 25 and the rotary joint 320 is sufficiently long. Namely, the urine discharge hose 330 extends backward almost horizontally from the urine receiving cup 25 and is then curved upward. Then, the urine discharge hose 330 is curved toward the front and then toward the rear, and finally connected to the rotary joint 320. The urine discharge hose 330 has a loop portion 330a constituted of the above curved portions and curved through almost 270°. Because of the loop portion 330a, urine tends to collect in the part of the urine discharge hose 330 between the urine receiving cup 25 and the rotary joint 320 (trap effect of the loop portion 330a). A urine sensor S2 is attached to the part where urine tends to collect.

By forming the loop portion 330a, the urine discharge hose 330 has a part which crosses over itself at an angle of about 90°. A holding clip 340 is provided at the crossover point. The holding clip 340 has two hose holding part 340a and 340b. The holding part 340a and 340b are holes extending perpendicular to each other as shown in FIG. 38 and FIG. 39. The urine discharge hose 330 is slidably inserted through the hose holding parts 340a and 340b. The holding clip 340 may be made of a synthetic resin, for example.

By changing the positions of the parts of urine discharge hose 330 extending through the holding clip 340, the position of the urine receiving cup 25 relative to the stool receiving cup 10 can be adjusted. Namely, by changing the position of the part of the urine discharge hose 330 extending almost horizontally with respect to the holding clip 340, the longitudinal position of the urine receiving cup 25 can be adjusted. Also, by changing the position of the part of the urine discharge hose 330 extending almost vertically with respect to the holding clip 340, the vertical position of the urine receiving cup 25 can be adjusted.

Although description has been made of the embodiments of this invention, it should be understood that this invention is not limited to the embodiments but can be modified in various ways. For example, the sensor units (400, 400B, 400C) can be used in various applications such as detection of the presence or absence or the amount of a substance in a piping system. The high-frequency oscillation circuit 410 and the detection circuit 420 are not limited to the ones shown in the embodiments but may be any known circuits. It should be understood that the object of this invention is to provide not only devices and methods specifically described but also devices and a methods substantially described as preferred and advantageous embodiments.

The invention claimed is:

1. A capacitance-coupled sensor configured to detect the presence or absence of a substance, comprising:
a sensor unit having a transmission electrode, a reception electrode capacitively couplable to said transmission electrode, and a shielding electrode interposed between said transmission electrode and said reception electrode for shielding the transmission electrode and the reception electrode from each other, a high-frequency oscillator interposed between said transmission electrode and said shielding electrode for applying a high-frequency voltage to said transmission electrode;

a detector interposed between said reception electrode and said shielding electrode for converting a high-frequency voltage outputted from said reception electrode into a DC voltage;

an excrement cup attachable to a patient for receiving at least excrement of said patient; and a stool discharge passage for discharging at least stool from said excrement cup with an in-cup opening which opens upward in said excrement cup, wherein said sensor unit is placed across said in-cup opening so that stool excreted by said patient can be received by the sensor unit and said stool on said sensor unit is passed through said sensor unit when said stool discharge passage is subjected to suction, and wherein said sensor unit is constituted of a plurality of conductive wires divided into first to third groups each having a plurality of conductive wires, said plurality of conductive wires including at least three conductive wires extending in parallel to each other at small intervals as a whole, a plurality of conductive wires in said first group serving as a plurality of transmission electrodes, a plurality of conductive wires in said second group serving as a plurality of reception electrodes, and a plurality of conductive wires in said third group serving as a plurality of shielding electrodes, said conductive wires serving as shielding electrodes being arranged between each of conductive wires serving as transmission electrodes and each of said conductive wires serving as reception electrodes, said conductive wires serving as transmission electrodes being electrically connected with each other at one end, said conductive wires serving as said reception electrodes being electrically connected with each other at one end, and said conductive wires serving as shielding electrodes being electrically connected with each other at one end an excrement cup attachable to a patient for receiving at least excrement of said patient.

2. The capacitance-coupled sensor as claimed in claim 1, wherein each of said conductive wires is coated with an insulating coating material.

3. The capacitance-coupled sensor as claimed in claim 1, further comprising spacer members provided at both longitudinal ends of said conductive wires for maintaining the intervals between said conductive wires.

4. The capacitance-coupled sensor as claimed in claim 1, wherein said high-frequency oscillator is a clock incorporated in a computer.

5. The capacitance-coupled sensor as claimed in claim 1, wherein said substance is a living body, excrement of a living body, gas, liquid, solid matter, powder, particulate matter or gelatinous substance.

* * * * *

UNITED STATES PATENT AND TRADEMARK OFFICE
CERTIFICATE OF CORRECTION

| | |
|---|---|
| PATENT NO. | : 7,387,619 B2 |
| APPLICATION NO. | : 10/488239 |
| DATED | : June 17, 2008 |
| INVENTOR(S) | : Teruo Kitamura |

Page 1 of 1

It is certified that error appears in the above-identified patent and that said Letters Patent is hereby corrected as shown below:

Column 24, lines 13-15 (claim 1, last 3 lines) delete "an excrement cup attachable to a patient for receiving at least excrement of said patient"

Signed and Sealed this

Nineteenth Day of January, 2010

David J. Kappos
*Director of the United States Patent and Trademark Office*